United States Patent
Schnermann et al.

(10) Patent No.: US 11,746,086 B2
(45) Date of Patent: *Sep. 5, 2023

(54) NON-AGGREGATING HEPTAMETHINE CYANINE FLUOROPHORES FOR IN VIVO IMAGING

(71) Applicant: The USA, as represented by the Secretary, Department of Health and Human Services, Bethesda, MD (US)

(72) Inventors: Martin John Schnermann, Rockville, MD (US); Michael Philip Luciano, Frederick, MD (US); Roger Rauhauser Nani, Frederick, MD (US)

(73) Assignee: The USA, as represented by the Secretary, Department of Health and Human Services, Bethesda, MD (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/179,217

(22) Filed: Feb. 18, 2021

(65) Prior Publication Data
US 2021/0198196 A1 Jul. 1, 2021

Related U.S. Application Data

(63) Continuation of application No. 16/969,902, filed as application No. PCT/US2019/018153 on Feb. 15, 2019, now Pat. No. 10,961,193.

(60) Provisional application No. 62/631,390, filed on Feb. 15, 2018.

(51) Int. Cl.
| | |
|---|---|
| *C07D 209/10* | (2006.01) |
| *A61K 49/00* | (2006.01) |
| *G01N 21/64* | (2006.01) |
| *G01N 33/533* | (2006.01) |
| *G01N 33/58* | (2006.01) |
| *C07D 403/12* | (2006.01) |
| *C09K 11/06* | (2006.01) |

(52) U.S. Cl.
CPC .......... *C07D 209/10* (2013.01); *A61K 49/006* (2013.01); *A61K 49/0032* (2013.01); *A61K 49/0058* (2013.01); *C07D 403/12* (2013.01); *C09K 11/06* (2013.01); *G01N 21/6428* (2013.01); *G01N 33/533* (2013.01); *G01N 33/582* (2013.01); *G01N 2021/6439* (2013.01)

(58) Field of Classification Search
CPC .... C09K 11/06; C07D 209/10; C07D 209/12; C07D 403/12; A61K 49/00; A61K 49/0032; A61K 49/0058; A61K 49/006; G01N 21/6428; G01N 33/533; G01N 33/582; G01N 2021/6439
USPC ............... 424/1.11, 1.65, 9.1, 9.6
See application file for complete search history.

(56) References Cited

U.S. PATENT DOCUMENTS

| | | | |
|---|---|---|---|
| 10,280,307 B2* | 5/2019 | Schnermann | C07D 209/12 |
| 10,561,729 B2 | 2/2020 | Schnermann et al. | |
| 10,876,003 B2* | 12/2020 | Schnermann | C07D 209/14 |
| 10,961,193 B2* | 3/2021 | Schnermann | G01N 33/582 |
| 2021/0100919 A1 | 4/2021 | Schnermann et al. | |

FOREIGN PATENT DOCUMENTS

| | | |
|---|---|---|
| WO | WO 2016/072984 A1 | 5/2016 |
| WO | WO 2017/027721 A1 | 2/2017 |
| WO | WO 2018/031448 A1 | 2/2018 |
| WO | WO 2019/040825 A1 | 2/2019 |
| WO | WO 2019/161091 A1 | 8/2019 |
| WO | WO 2020/041743 A1 | 2/2020 |

OTHER PUBLICATIONS

Cha et al., "A chemically stable fluorescent marker of the ureter," *Bioorg. Med. Chem. Lett.*, vol. 28(16), pp. 2741-2745 (2018).
Choi et al., "Synthesis and In Vivo Fate of Zwitterionic Near-Infrared Fluorophores," *Angew Chem. Int. Ed. Engl.*, author manuscript, 12 pages, published in final edited form Jul. 4, 2011, 50(28):6258-6263.
Choi et al., "Targeted zwitterionic near-infrared fluorophores for improved optical imaging," *Nat Biotechnol.* author manuscript, 16 pages, published in final edited form Feb. 2013, doi:10.1038/nb6.2468.
Gorka et al., "A Near-IR Uncaging Strategy Based on Cyanine Photochemistry," *Journal of American Chemical Society*, 7 pages (Sep. 11, 2014).
Gorka et al., "Harnessing cyanine photooxidation: from slowing photobleaching to near-IR uncaging," *Current Opinion in Chemical Biology*, 33:117-125 (2016).
International Search Report and Written Opinion dated Apr. 23, 2019, issued by the European Patent Office in corresponding application PCT/US2019/018153, filed Feb. 15, 2019.
Luciano, "Bright, Stable Heptamethine Cyanine Fluorophores for In Vivo Imaging," NIH Research Festival: Chemical Biology Symposium, 14 pages, (Sep. 13, 2018).
Matsui et al., "Real-Time Near-Infrared Fluorescence-Guided Identification of the Ureters using Methylene Blue," *Surgery*, author manuscript 16 pages, published in final edited form Jul. 2010, 148(1):78-86.
Nani et al., "Electrophile-Integrating Smiles Rearrangement Provides Previously Inaccessible C4'-O-Alkyl Heptamethine Cyanine Fluorophores," *Org. Lett.*, 17:302-305 (Jan. 6, 2015).
Nani et al., "In Vivo Activation of Duocarmycin—Antibody Conjugates by Near-Infrared Light," *ACS Cent. Sci.*, 3:329-337 (2017).

(Continued)

*Primary Examiner* — D. L. Jones
(74) *Attorney, Agent, or Firm* — Klarquist Sparkman, LLP

(57) ABSTRACT

Heptamethine cyanine fluorophore conjugates and conjugate precursors are disclosed. Methods of using the conjugates and conjugate precursors are also disclosed. The disclosed conjugates are neutral zwitterionic molecules and exhibit little or no aggregation.

19 Claims, 13 Drawing Sheets

(56) References Cited

OTHER PUBLICATIONS

Nani et al., "Near-IR Light-Mediated Cleavage of Antibody—Drug Conjugates Using Cyanine Photocages," *Angew. Chem. Int. Ed.*, 54:13635-13638 (2015).
Sato et al., "Effect of charge localization on the in vivo optical imaging properties of near-infrared cyanine dye/monoclonal antibody conjugates," *Mol. BioSyst.*, 12:3046-3056 (2016).
Sato et al., "Role of Fluorophore Charge on the In Vivo Optical Imaging Properties of Near-Infrared Cyanine Dye/Monoclonal Antibody Conjugates," *Bioconjugate Chem.*, 27:404-413 (Oct. 7, 2015).

\* cited by examiner

NON-AGGREGATING HEPTAMETHINE CYANINE FLUOROPHORES FOR IN VIVO IMAGING

CROSS REFERENCE TO RELATED APPLICATIONS

This is a continuation of U.S. application Ser. No. 16/969,902, filed Aug. 13, 2020, now U.S. Pat. No. 10,961,193, which is the U.S. National Stage of International Application No. PCT/US2019/018153, filed Feb. 15, 2019, which was published in English under PCT Article 21(2), which in turn claims the benefit of the earlier filing date of U.S. Provisional Application No. 62/631,390, filed Feb. 15, 2018, each of which is incorporated by reference herein in its entirety.

ACKNOWLEDGMENT OF GOVERNMENT SUPPORT

This invention was made with government support under project number Z01 ZIA BC011506 by the National Institutes of Health, National Cancer Institute. The government has certain rights in the invention.

FIELD

This disclosure concerns heptamethine cyanine fluorophore conjugates and conjugate precursors. Methods of making and using the fluorophore conjugates and conjugate precursors also are disclosed.

BACKGROUND

Near-infrared (NIR) wavelengths can facilitate the visualization of biological processes in vivo. The use of fluorophore-labeled biomacromolecules is an enduring strategy employed across the spectrum of fundamental to applied biomedical science. However, fluorophore conjugation often alters the properties of both the fluorophore and the molecule to which it is attached. Specifically, important parameters such as brightness, target binding, in vivo stability and pharmacokinetics (PK) are often impacted. An important component of these issues is the formation of dye aggregates. In particular, H-aggregates, which are characterized by the appearance of a hypsochromic (blue-shifted) absorption band and a reduction in fluorescence intensity, are a common consequence of fluorophore bioconjugation.

A common strategy to avoid aggregation is the introduction of multiple anionic sulfonate groups. However, while dye sulfonation is a highly successful strategy for fluorophores in the visible range, persulfonated near-infrared (NIR) fluorophores are still prone to the formation of aggregates at even moderate labeling density. Since NIR fluorophores intrinsically less emissive than their counterparts in the visible range, strategies to circumvent the formation of non-emissive aggregates remain a pressing need.

SUMMARY

This disclosure concerns heptamethine cyanine conjugates and conjugate precursors, as well as methods of making and using the conjugates and conjugate precursors. Advantageously, some embodiments of the disclosed heptamine cyanine conjugates are highly resistant to aggregation when conjugated to a targeting agent, e.g., a biomolecule such as an antibody or receptor ligand.

In some embodiments, a conjugate or conjugate precursor, or a stereoisomer thereof, has a structure according to Formula IA:

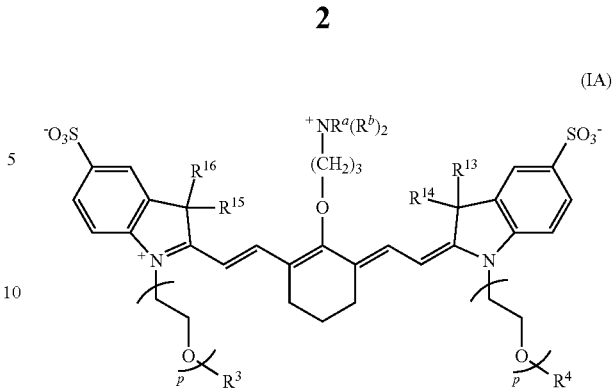

(IA)

wherein p is 2, 3, or 4; $R^a$ is $(R^1)_q C(O)R^c$ where q is 1, 2, 3, 4, 5, 6, 7, 8, 9, or 10, each $R^b$ independently is $C_1$-$C_5$ aliphatic; $R^c$ is a targeting agent-containing group,

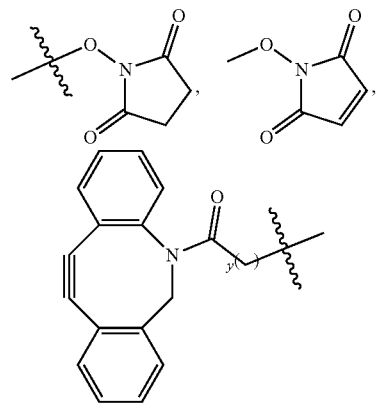

where y is an integer ≥ 1, or —OH; $R^1$ is —$CR^2_2$ where each $R^2$ independently is H, halo, optionally substituted aliphatic, or optionally substituted aryl; $R^3$ and $R^4$ independently are aliphatic; and $R^{13}$ to $R^{16}$ independently are aliphatic. In certain embodiments, each $R^b$ is the same; $R^3$ and $R^4$ are the same; and $R^{13}$-$R^{16}$ are the same. In any of the foregoing embodiment, q may be 2, 3, or 4. In any of the foregoing embodiments, $R^a$ may be —$(CH_2)_q C(O)R^c$ where q is 2, 3, or 4.

In some embodiments, $R^c$ is a targeting agent-containing group, and the conjugate has a structure according to Formula IIA where x is 2, 3, 4, 5, 6, 7, or 8:

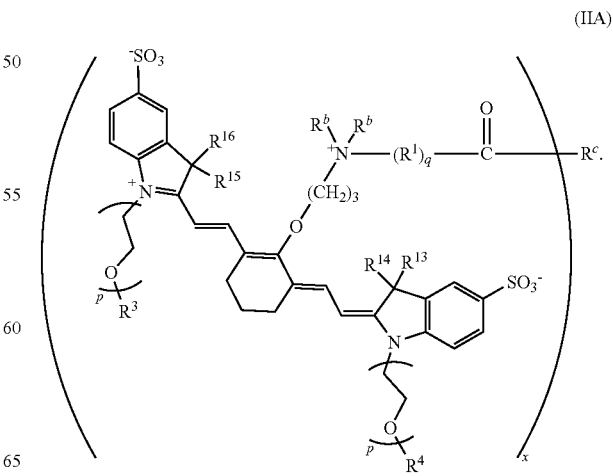

(IIA)

In any of the foregoing embodiments, (i) $R^3$ and $R^4$ may be methyl; or (ii) $R^{13}$-$R^{16}$ may be methyl; or (iii) both (i) and (ii). In any of the foregoing embodiments, each $R^b$ may be methyl.

In some embodiments, $R^a$ is $(CH_2)_3C(O)R^c$ where $R^c$ is a targeting agent-containing group and the conjugate is:

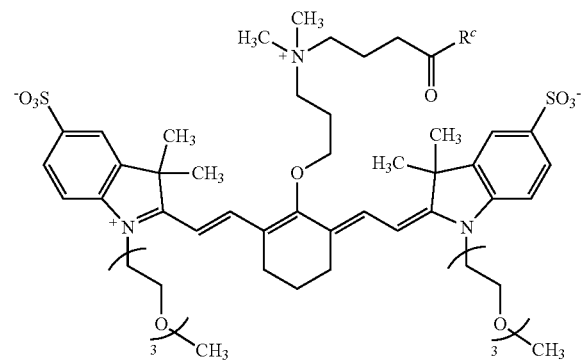

In any of the foregoing embodiments, $R^c$ may be N(H)Ab where Ab is an antibody.

In one embodiment, $R^c$ is

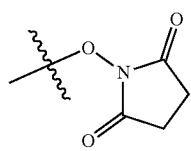 [SMILES: *ON1C(=O)CCC1=O]

and the conjugate precursor is:

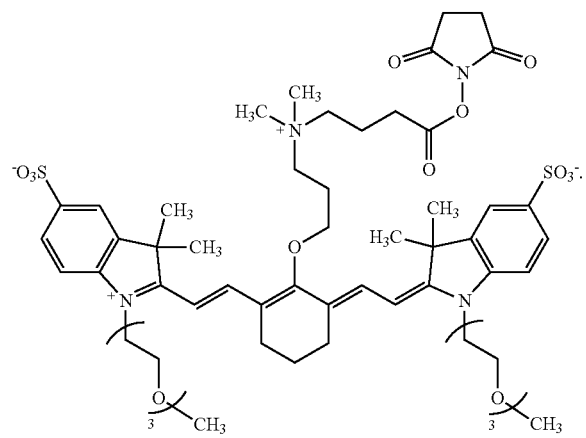

Embodiments of the disclosed conjugates are useful in fluorescence applications. In some embodiments, a method includes: contacting a biological sample including, or suspected of including, a target with a disclosed conjugate, wherein $R^c$ is a targeting agent-containing group, the targeting agent capable of recognizing and binding to the target; subsequently irradiating the biological sample with a quantity of light having a selected wavelength and selected intensity to induce fluorescence of the conjugate; and detecting fluorescence of the irradiated biological sample, wherein fluorescence indicates presence of the target in the biological sample. In some embodiments, the targeting agent is an antibody.

In some embodiments, contacting the biological sample with the conjugate is performed in vivo by administering the conjugate or a pharmaceutical composition comprising the conjugate to a subject. In such embodiments, irradiating the biological sample comprises irradiating a target area of the subject; and detecting fluorescence comprises obtaining an image of the irradiated target area, wherein fluorescence in the image indicates presence of the target in the target area. In certain embodiments, the target is a tumor and the target area is an area in which the tumor is located. In some examples, the targeting agent is capable of recognizing and binding to cells of the tumor, irradiating the biological sample comprises irradiating the target area of the subject, and detecting fluorescence indicates presence of tumor cells in the target area, and the method further includes excising fluorescent tumor cells from the target area.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
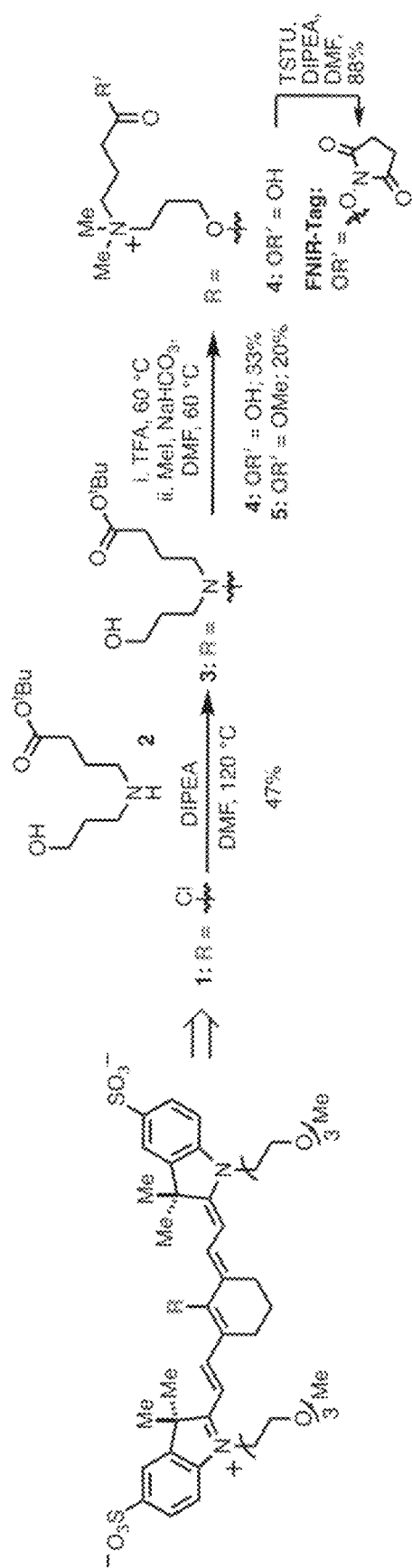
FIG. 1 is an exemplary scheme for synthesizing one embodiment of a conjugate precursor as disclosed herein.

This disclosure concerns heptamethine cyanine conjugates and conjugate precursors, as well as methods of making and using the conjugates and conjugate precursors. Advantageously, some embodiments of the disclosed heptamine cyanine conjugates are highly resistant to aggregation when conjugated to a targeting agent, e.g., a biomolecule such as an antibody or receptor ligand. In certain embodiments, the conjugates also exhibit exceptionally bright in vivo signals when compared to conventional heptamethine cyanines.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkyl: A hydrocarbon group having a saturated carbon chain. The chain may be branched, unbranched, or cyclic (cycloalkyl). Unless otherwise specified, the term alkyl encompasses substituted and unsubstituted alkyl.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In avian and reptilian species, IgY antibodies are equivalent to mammalian IgG.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

The structure of IgY antibodies is similar to the structure of mammalian IgG, with two heavy ("nu" chains; approximately 67-70 kDa) and two light chains (22-30 kDa). The molecular weight of an IgY molecule is about 180 kDa, but it often runs as a smear on gels due to the presence of about 3% carbohydrate. Heavy chains (H) of IgY antibodies are composed of four constant domains and one variable domain, which contains the antigen-binding site.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999). As used herein, the term "antibodies" includes antibodies comprising one or more unnatural (i.e., non-naturally occurring) amino acids (e.g., p-acetyl-phenylalanine) to facilitate site-specific conjugation.

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. As used herein, a "target antigen" is an antigen (including an epitope of the antigen) that is recognized and bound by a targeting agent. "Specific binding" does not require exclusive binding. In some embodiments, the antigen is obtained from a cell or tissue extract. In some embodiments, the target antigen is an antigen on a tumor cell. An antigen need not be a full-length protein. Antigens contemplated for use include any immunogenic fragments of a protein, such as any antigens having at least one epitope that can be specifically bound by an antibody.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

Biological sample: As used herein, a "biological sample" refers to a sample obtained from a subject (such as a human or veterinary subject) or other type of organism, such as a plant, bacteria or insect. Biological samples from a subject include, but are not limited to, cells, tissue, serum, blood, plasma, urine, saliva, cerebral spinal fluid (CSF) or other bodily fluid. In particular examples of the method disclosed herein, the biological sample is a tissue sample.

Conjugate: Two or more moieties directly or indirectly coupled together. For example, a first moiety may be covalently coupled to a second moiety. Indirect attachment is possible, such as by using a "linker" (a molecule or group of atoms positioned between two moieties).

Effective amount: As used herein, the term "effective amount" refers to an amount sufficient for detection in a biological sample, e.g., by fluorescence.

Epitope: An antigenic determinant Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

H-aggregation: Aggregation (the formation of multiple molecules into a cluster) that leads to a hypsochromic, or spectral blue, shift with low or no fluorescence.

Halogen: The terms halogen and halo refer to fluorine, chlorine, bromine, iodine, and radicals thereof.

Ligand: A molecule that binds to a receptor, having a biological effect.

Near-infrared (near-IR, NIR): Wavelengths within the range of 650-2500 nm. Unless otherwise specified, the terms "near-infrared" and "NIR" as used herein refer to wavelengths within the range of 650-900 nm.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more targeting agent-drug conjugates as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed conjugate, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Precursor: An intermediate compound. A precursor participates in a chemical reaction to form another compound. As used herein, the term "conjugate precursor" refers to a compound including a functional group useful for forming a conjugate, e.g., a conjugate of a heptamethine cyanine molecule and a targeting agent.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, receptor/ligand, nucleic acid strand/complementary nucleic acid strand, substrate/enzyme, inhibitor/enzyme, carbohydrate/lectin, biotin/avidin (such as biotin/streptavidin), and virus/cellular receptor.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Sulfonate-containing group: A group including $SO_3^-$. The term sulfonate-containing group includes —$SO_3^-$ and —$RSO_3^-$ groups, where R is substituted or unsubstituted alkyl, substituted or unsubstituted heteroalkyl, substituted or unsubstituted aryl, or substituted or unsubstituted heteroaryl.

Target: An intended molecule to which a disclosed conjugate comprising a targeting agent is capable of specifically binding. Examples of targets include proteins and nucleic acid sequences present in tissue samples. A target area is an area in which a target molecule is located or potentially located.

Targeting agent: An agent that promotes preferential or targeted delivery to a target site, for example, a targeted location in a subject's body, such as a specific organ, organelle, physiologic system, tissue, or site of pathology such as a tumor, area of infection, or area of tissue injury. Targeting agents function by a variety of mechanisms, such as selective concentration in a target site or by binding to a specific binding partner. Suitable targeting agents include, but are not limited to, proteins, polypeptides, peptides, glycoproteins and other glycoslyated molecules, oligonucleotides, phospholipids, lipoproteins, alkaloids, steroids, and nanoparticles. Exemplary targeting agents include antibodies, antibody fragments, affibodies, aptamers, albumin, cytokines, lymphokines, growth factors, hormones, enzymes, immune modulators, receptor proteins, antisense oligonucleotides, avidin, nanoparticles, and the like. Particularly useful of targeting agents are antibodies, nucleic acid sequences, and receptor ligands, although any pair of specific binding partners can be readily employed for this purpose.

II. CONJUGATES AND CONJUGATE PRECURSORS

Disclosed herein are embodiments of conjugates and conjugate precursors comprising a heptamethine cyanine fluorophore and a targeting agent or a functional group suitable for forming a conjugate with a targeting agent. The conjugates and conjugate precursors have a chemical structure according to Formula I or a stereoisomer thereof.

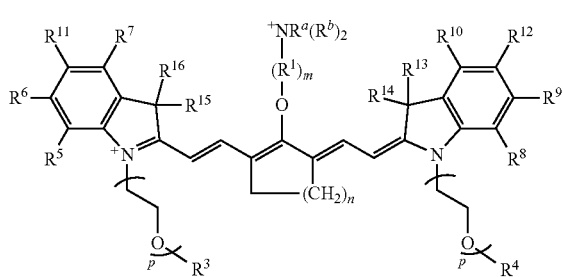
(I)

With respect to Formula I, m is 3, 4, or 5; n is 1, 2, or 3; and each p independently is 1, 2, 3, 4, 5, 6, 7, 8, 9, or 10. $R^1$ is —$CR^2{}_2$— where each $R^2$ independently is H, halo, optionally substituted aliphatic, or optionally substituted aryl. $R^3$ and $R^4$ independently are aliphatic. $R^5$ to $R^{10}$ independently are H or aliphatic. $R^{11}$ and $R^{12}$ independently are a sulfonate-containing group. $R^{13}$ to $R^{16}$ independently are aliphatic. $R^a$ is —$(R^1)_qC(O)R^c$ where q is 1, 2, 3, 4, 5, 6, 7, 8, 9, or 10, and $R^c$ is a targeting agent-containing group,

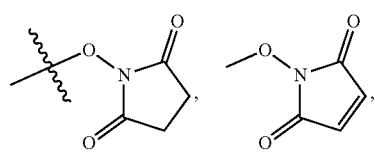

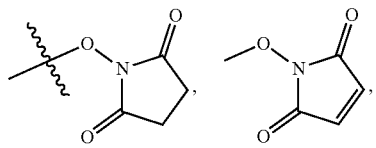

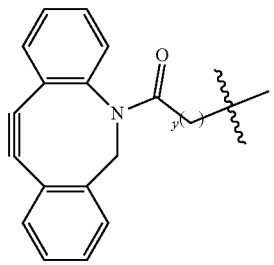

where y is an integer≥1, or OH. Each $R^b$ independently is $C_1$-$C_5$ aliphatic. In any of the foregoing embodiments, aliphatic may be $C_1$-$C_5$ aliphatic.

In some embodiments, m, n, p, $R^a$, and $R^c$ are as above; $R^1$ is —$CR^2{}_2$— where each $R^2$ independently is H, halo, optionally substituted alkyl, or optionally substituted aryl; $R^3$ and $R^4$ independently are alkyl; $R^5$ to $R^{10}$ independently are H or alkyl; $R^{11}$ and $R^{12}$ are —$SO_3{}^-$; $R^{13}$ to $R^{16}$ independently are alkyl; and each $R^b$ independently is $C_1$-$C_5$ alkyl. In any of the foregoing embodiments, alkyl may be $C_1$-$C_5$ alkyl.

In some embodiments, the molecule is a conjugate and $R^c$ is a targeting agent-containing group. The targeting agent may be an antibody, a peptide, a protein, an amino acid, a nucleoside, a nucleotide, a nucleic acid, an oligonucleotide, a carbohydrate, a lipid, a hapten, or a receptor ligand.

In certain embodiments, the targeting agent is an antibody. $R^c$ may be, for example, —N(H)Ab where Ab is the antibody. In some embodiments, the antibody is capable of recognizing and binding to a tumor biomarker, such as a protein only found in or on tumor cells or to a cell-surface receptor associated with one or more cancers. For example, panitumumab is a human monoclonal antibody that recognizes and binds to human epidermal growth factor receptor 1 (HER1); HER1 is overexpressed in numerous tumor types and is also associated with some inflammatory diseases. Trastuzumab and pertuzumab are monoclonal antibodies that bind to the HER2/neu receptor, which is over-expressed in some breast cancers. Brentuximab is a monoclonal antibody that targets a cell-membrane protein CD30, which is expressed in classical Hodgkin lymphoma and systemic anaplastic large cell lymphoma.

In some embodiments, the molecule is a conjugate precursor and $R^c$ is

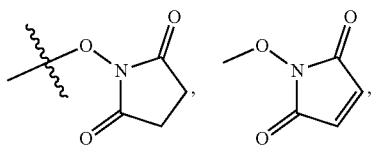

In some embodiments, the conjugate or conjugate precursor has a structure according to Formula IB:

(IB)

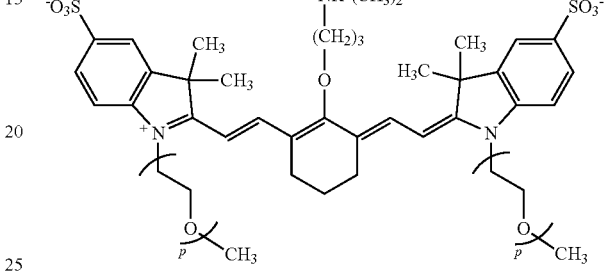

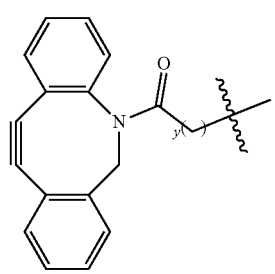

where y is an integer≥1, or OH.

The conjugate or conjugate precursor may be symmetrically substituted. For example, in some embodiments, $R^3$ and $R^4$ are the same, $R^5$ and $R^8$ are the same, $R^6$ and $R^9$ are the same, $R^7$ and $R^{10}$ are the same, $R^{11}$ and $R^{12}$ are the same, and $R^{13}$-$R^{16}$ are the same.

In any of the foregoing embodiments, $R^5$-$R^{10-}$ may be H, and $R^{11}$ and $R^{12}$ may be sulfonate ($-SO_3^-$). In any of the foregoing embodiments, (i) n may be 2, or (ii) p may be 2, 3, or 4, or (iii) q may be 2, 3, or 4, or (iv) any combination of (i), (ii), and (iii).

In some embodiments, the conjugate or conjugate precursor has a structure according to Formula IA.

In any of the foregoing embodiments, $R^a$ may be $-(CH_2)_q C(O)R^c$ where q is 1, 2, 3, 4, 5, 6, 7, 8, 9, or 10. In certain embodiments, q is 2, 3, or 4.

In one embodiment, the compound is a conjugate precursor where $R^c$ includes a succinimidyl group and the conjugate precursor is FNIR-Tag:

(FNIR-Tag)

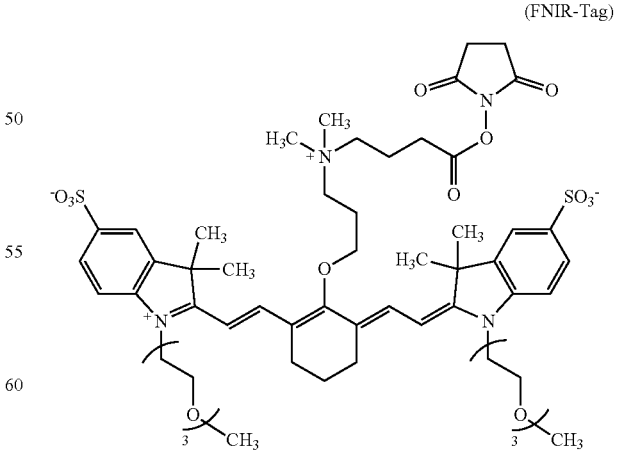

(IA)

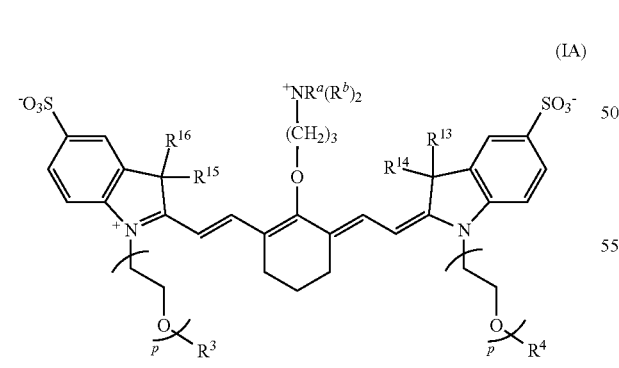

With respect to Formula IA, $R^3$, $R^4$, $R^{13}$-$R^{16}$, $R^a$, and $R^b$ are as previously defined; and p is 2, 3, or 4.

In any of the foregoing embodiments, (i) $R^3$ and $R^4$ may be methyl, or (ii) $R^{13}$-$R^{16}$ may be methyl, or (iii) both (i) and (ii). In any of the foregoing embodiments, each $R^b$ may be methyl.

In some embodiments, the compound is a conjugate and $R^c$ is a targeting agent-containing group. In certain examples, $R^a$ is $(CH_2)_3C(O)R^c$ and the conjugate is:

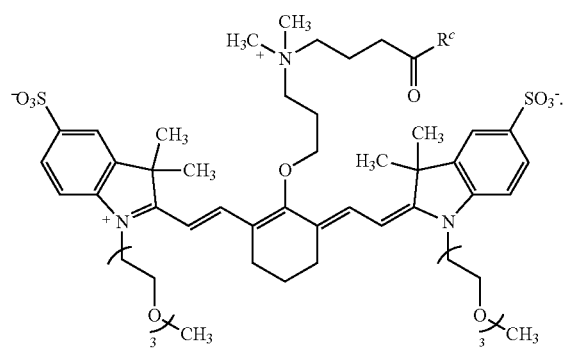

In some examples, $R^c$ is N(H)Ab where Ab is an antibody. In other examples, $R^c$ comprises a peptide, a nucleic acid, or a nanoparticle.

In some embodiments, when $R^c$ is a targeting agent-containing group as disclosed herein, more than one heptamethine cyanine may be conjugated to each targeting agent. For example, the conjugate may have a degree of labeling (DOL) from 1-8, such as from 1-6, from 1-4, or from 2-4, wherein the DOL is the number of heptamethine cyanine moieties conjugated to the targeting agent. When the degree of labeling is 2 or more, the conjugate may have a structure according to Formula II, IIA, or IIB, where x is 2, 3, 4, 5, 6, 7, or 8:

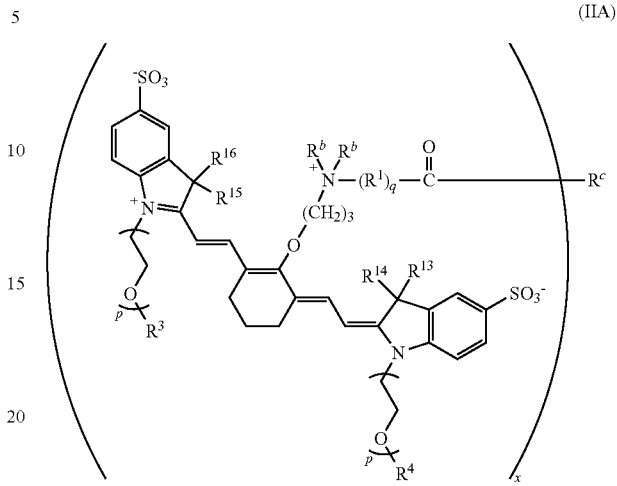

(IIA)

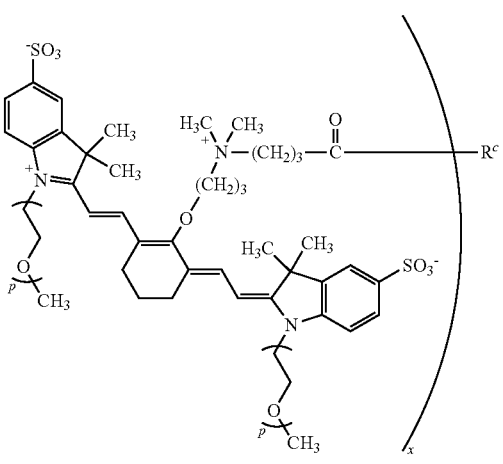

(II)

(IIB)

For example, when x is 3, the conjugate may have a structure:

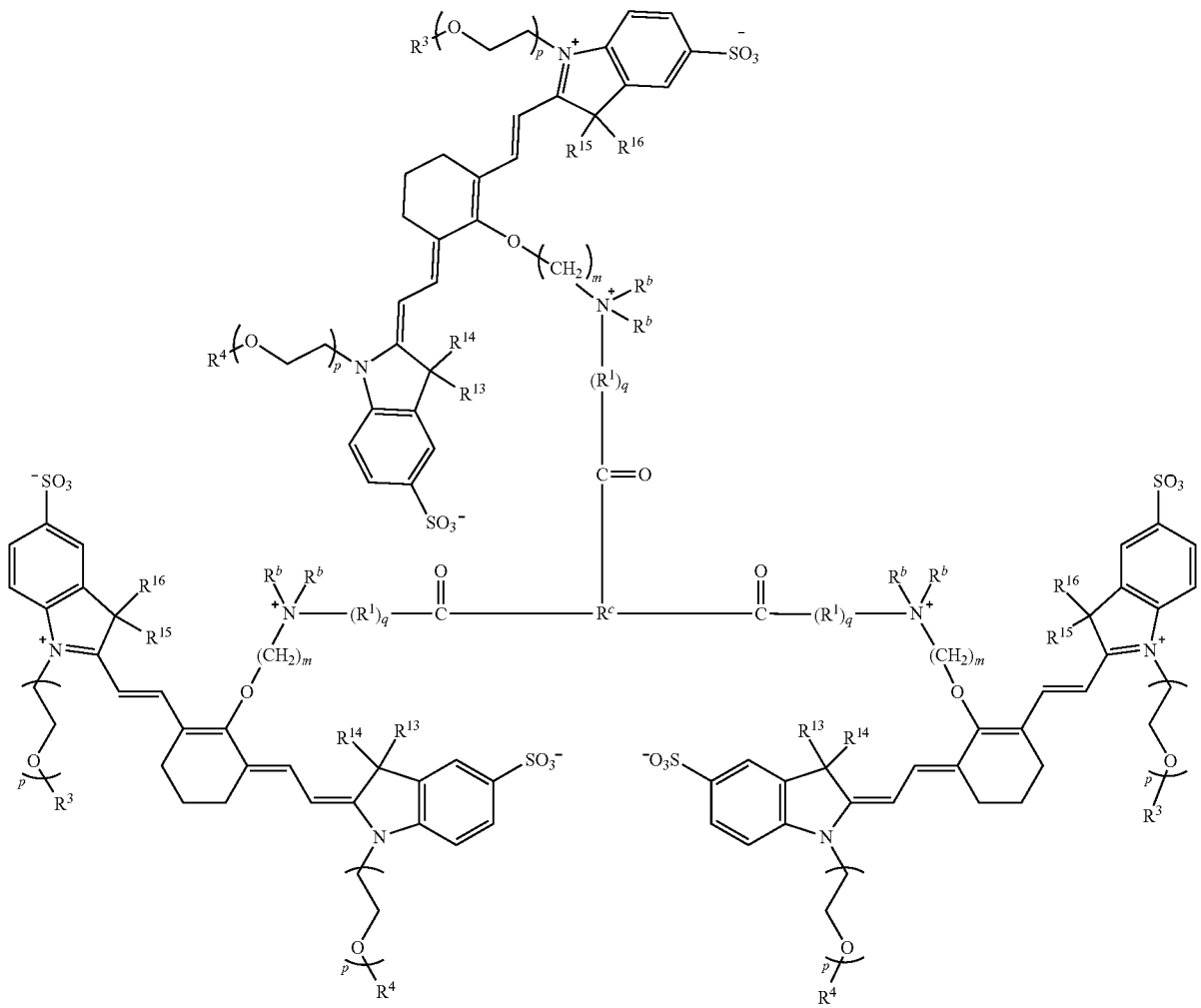

In the foregoing conjugates, $R^c$ may be any targeting agent as disclosed herein. In some examples, $R^c$ is —N(H)Ab where Ab is an antibody. In other examples, $R^c$ comprises a peptide, a nucleic acid, or a nanoparticle.

As with many fluorophores, heptamethine cyanines are prone to forming non-emissive aggregates upon conjugation to a targeting agent. Persulfonation strategies have been employed in the prior art with only partial success. However, some embodiments of the disclosed conjugates advantageously exhibit little or no aggregation. A combination of the short polyethylene glycol chains on the indolenine nitrogens and a substituted quaternary amine alkyl ether at the C4' position, resulting in a net-neutral zwitterionic dye, provides highly aggregation-resistant fluorophores. In some embodiments, symmetrical conjugates as disclosed herein can be prepared in a concise sequence, label monoclonal antibodies efficiently at neutral pH, and exhibit no evidence of H-aggregation at even high labeling density. In certain embodiments, the conjugates also exhibit exceptionally bright in vivo signals when compared to conventional heptamethine cyanines, including persulfonated heptamethine cyanines, such as the commercially available IRDye®-800CW fluorophore.

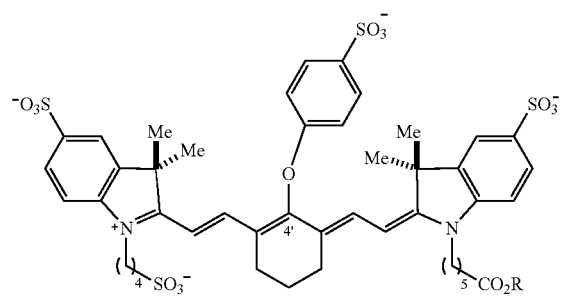

IRDye®-800CW fluorophore

In certain examples, antibody conjugates of FNIR-Tag exhibited superior tumor uptake and brightness when compared to a similarly labeled IRDye®-800CW conjugate in an in vivo imaging study in mice bearing EGFR+ tumors. Additionally, certain embodiments of the disclosed conjugates show reduced liver uptake compared to conventional heptamethine cyanine conjugates, such as IRDye®-800CW-based conjugates. Overall, embodiments of the disclosed conjugates and conjugate precursors provide excellent properties for complex and/or high-density labeling applications.

III. SYNTHESIS

Embodiments of the disclosed conjugates and conjugate precursors are synthesized from cyanine fluorophores in a short, scalable (up to 0.5 g) synthetic sequence and can be functionalized for a variety of applications. FIG. 1 shows an exemplary synthesis scheme for preparation of FNIR-Tag, a conjugate precursor including a conjugatable succinimidyl group Amine 2 (synthesized in three steps from commercial materials as described in Example 1) is reacted with 4'-chloroheptamethine cyanine 1 in the presence of N,N-diisopropylethylamine (DIPEA) to provide a deep blue C4'-N-linked heptamethine cyanine 3. In a one-pot reaction, FNIR-Tag is prepared by stirring heptamethine cyanine 3 in trifluoroacetic acid at 60° C., thereby removing the t-butyl ester group and inducing a C4' N- to O-transposition. A general N- to O-transposition reaction is shown below where x is an integer, R is alkyl, heteroalkyl, aryl, or heteroaryl, Y is hydroxyl, E is an electrophile, and B is a base.

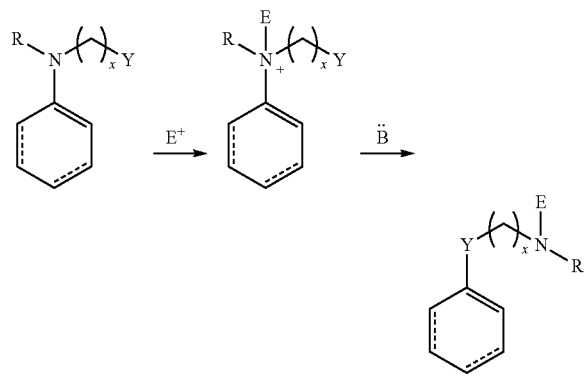

Subsequent exhaustive alkylation with excess NaHCO$_3$ and methyl iodide in N,N-dimethylformamide (DMF) forms carboxylic acid 4 and methyl ester 5 in yields of 20-30%. The methyl ester 5 is saponified to produce additional carboxylic acid 4. For future conjugation, the carboxylic acid 4 is converted to a conjugatable group. In the scheme of FIG. 1, the carboxylic acid 4 is converted under standard conditions to an N-hydroxysuccinimide ester, referred to herein as FNIR-Tag.

Embodiments of the disclosed conjugate precursors are conjugated to targeting agents by conventional methods known to those of skill in the art of preparing molecular conjugates. For example, FNIR-Tag is conjugated to an antibody by mixing the conjugate precursor and the antibody, and the resulting solution is incubated (e.g., at room temperature) for a period of time sufficient to allow conjugation. In one example, a 10 mM solution of FNIR-Tag in DMSO was mixed with phosphate-buffered saline (PBS) and combined with a 20 mg/mL solution of panitumumab in PBS. The combined solution was incubated for one hour at room temperature. In some embodiments, the conjugate precursor is present at a molar excess to the antibody to provide a degree of labeling (DOL) greater than 1. For example, the conjugate precursor may be combined with the antibody in a molar excess of 2-2.5 to provide an average DOL of 2.

IV. PHARMACEUTICAL COMPOSITIONS

This disclosure also includes pharmaceutical compositions comprising at least one conjugate as disclosed herein. Some embodiments of the pharmaceutical compositions include a pharmaceutically acceptable carrier and at least one conjugate. Useful pharmaceutically acceptable carriers and excipients are known in the art.

The pharmaceutical compositions comprising one or more conjugates may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as polyethoxylated castor oil, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the conjugate(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the conjugate may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some conjugate formulations may be dried, e.g., by spray-drying with a disaccharide, to form conjugate powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, polyethoxylated castor oil, or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal and vaginal routes of administration, the conjugate(s) may be formulated as solutions (for retention enemas) suppositories or ointments containing conventional suppository bases such as cocoa butter or other glycerides.

For nasal administration or administration by inhalation or insufflation, the conjugate(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

Certain embodiments of the pharmaceutical compositions comprising conjugates as described herein may be formulated in unit dosage form suitable for individual administration of precise dosages. The pharmaceutical compositions may, if desired, be presented in a pack or dispenser device which may contain one or more unit dosage forms containing the conjugate. The pack may, for example, comprise metal or plastic foil, such as a blister pack. The pack or dispenser device may be accompanied by instructions for administration. The amount of conjugate administered will depend at least in part on the subject being treated, the target (e.g., the size, location, and characteristics of a tumor), and the manner of administration, and is known to those skilled in the art. Within these bounds, the formulation to be administered will contain a quantity of the conjugate disclosed herein in an amount effective to be detectable (e.g., by fluorescence imaging) when the conjugate is irradiated with NIR light.

In some embodiments, the pharmaceutical composition includes a second therapeutic agent other than the conjugate. The second agent may be, for example, an anti-tumor agent or an angiogenesis inhibitor.

V. USES

Embodiments of the disclosed conjugates are suitable for in vivo, ex vivo, or in vitro use. Advantageously, the conjugate is fluorescent when irradiated with targeted application of an effective quantity of light having a selected wavelength and a selected intensity to induce fluorescence. When the conjugate has a DOL greater than one, fluorescence advantageously is increased compared to a conjugate with a DOL of one.

A biological sample may be contacted in vivo, ex vivo, or in vitro with a conjugate as disclosed herein. Following contact with the conjugate, the biological sample is irradiated with near-IR radiation to induce fluorescence. In some embodiments, a period of time is allowed to lapse between administration of the conjugate and application of near-IR radiation, thereby providing time for the conjugate to accumulate at and bind to the target site. The period of time may be several hours to several days, such as from 1-7 days or from 12 hours-2 days.

In some embodiments, the conjugate comprises a targeting agent capable of recognizing and binding directly or indirectly, in vitro, in vivo, or ex vivo, to a target (e.g., an antigen or a receptor) present or suspected of being present in the biological sample. In one embodiment, the biological sample is visualized under conditions suitable to produce near-IR fluorescence if the conjugate is present in the biological sample. Fluorescence also confirms presence of the target in the biological sample. Excess unbound conjugate may be removed from the biological sample (e.g., by washing a tissue sample) prior to visualizing the sample to detect fluorescence.

In one non-limiting example, a biological sample (e.g., a tissue sample) that may comprise a target is contacted with a conjugate comprising an antibody capable of recognizing and binding to the target. In another non-limiting example, a biological sample that may comprise a target is combined with a first antibody capable of recognizing and binding to the target; subsequently, the biological sample is contacted with a conjugate comprising an anti-antibody antibody. In another non-limiting example, the biological sample is contacted with a conjugate comprising a ligand capable of binding to a receptor. For instance, substituent $R^c$ may comprise a receptor ligand capable of binding to a receptor on a cell surface.

In some embodiments, an effective amount of a conjugate as disclosed herein, or a pharmaceutical composition comprising the conjugate, is administered to a subject. An effective amount of the conjugate is an amount sufficient to be detectable (e.g., by fluorescence imaging) when irradiated by targeted application of an effective quantity of light having a wavelength in the near-infrared range and a selected intensity to a targeted portion of the subject. The effective amount of the conjugate may be reduced when the conjugate has a DOL greater than one since the conjugate may produce greater fluorescence when irradiated.

In certain embodiments, the light source provides light having a wavelength within a range of 650-900 nm, such as a wavelength from 650-800 nm or 680-750 nm, and an intensity of 1-1000 mW/cm$^2$, such as 300-700 mW/cm$^2$. In one embodiment, the light has a wavelength of 690 nm and an intensity of 500 mW/cm$^2$. In another embodiment, the light has a wavelength of 740 nm and an intensity of 500 mW/cm$^2$.

In one embodiment, the subject has a tumor and the conjugate comprises a targeting agent capable of recognizing and binding to an antigen or ligand-binding receptor of the tumor. Suitable tumors include, but are not limited to, solid tumor masses, such as intraperitoneal tumors (e.g., ovarian, prostate, colorectal), breast tumors, or head/neck tumors. The targeting agent may be, for example, an antibody that recognizes and binds to the tumor antigen. An effective amount of the conjugate, a pharmaceutically acceptable salt thereof, or a pharmaceutical composition comprising the conjugate, is administered to the subject by any suitable means including, but not limited to, parenteral, intravenous, subcutaneous, oral, rectal, vaginal, or topical administration. The administered conjugate is irradiated by targeted application of NIR light to an area proximate a location of the tumor.

Figure 2:
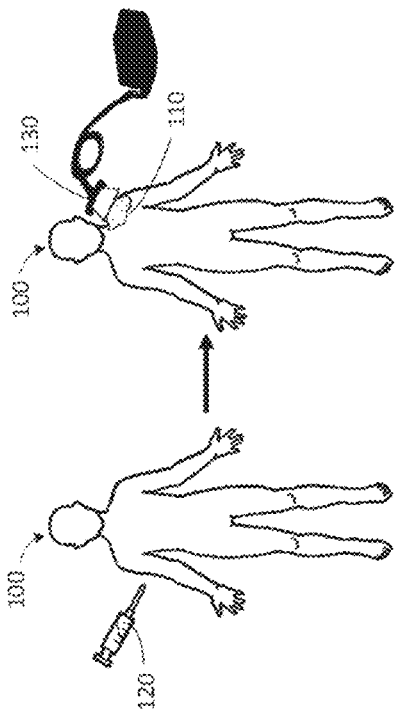
FIG. 2 is a schematic diagram illustrating one embodiment of a method for using the disclosed heptamethine cyanine conjugates by injection of the conjugate into a subject followed by targeted delivery of light of a desired wavelength to a targeted area of the subject.

With reference to FIG. 2, a subject 100 with a tumor 110 may be administered a conjugate comprising an antibody or ligand capable of recognizing and binding to an antigen or receptor on a tumor cell surface. Administration of the conjugate to the subject may facilitate visualization and/or localization of the tumor. In the example shown in FIG. 2, the conjugate 120 is administered via intravenous injection. A period of time is allowed to elapse during which the conjugate preferentially accumulates at the tumor site as the antibody or ligand moiety binds to the tumor. A target portion of the subject subsequently is selectively irradiated with an effective amount of NIR light energy of a desired wavelength using an external light applicator 130. The light applicator 130 applies the photoactivation energy to a target area limited to the region of the tumor 110, thereby enabling visualization of the tumor. In some examples, the tumor site is exposed by surgical incision prior to exposing the tumor to light. The tumor is excised using the area of fluorescence as guidance.

In one embodiment, at least a portion of the tumor is excised from the subject before administering the effective amount of the conjugate or the pharmaceutical composition comprising the conjugate to the subject. In an independent embodiment, the effective amount of the conjugate or the pharmaceutical composition comprising the conjugate is administered to the subject before surgical excision of the tumor or a portion thereof.

A therapeutically effective amount of a second agent may be co-administered with the conjugate. The conjugate and the second agent may be administered either separately or together in a single composition. The second agent may be administered by the same route or a different route. If administered concurrently, the conjugate and the second agent may be combined in a single pharmaceutical composition or may be administered concurrently as two pharmaceutical compositions. The second agent may be, for example, a chemotherapeutic agent, such as an anti-tumor agent or an angiogenesis inhibitor, an anti-inflammatory agent, an anti-infective agent, an anti-oxidant, or any combination thereof.

In another embodiment, an in vitro or ex vivo evaluation may be performed to determine whether a particular conjugate as disclosed herein will effectively bind to a tissue sample obtained from a subject. The conjugate comprises a targeting agent at $R^c$ thought to be capable of binding to or associating with the target molecule. In one non-limiting example, $R^c$ comprises a receptor ligand or antibody capable of binding to a target receptor. The conjugate is combined with the tissue sample, and the sample is subsequently irradiated with an effective amount of near-IR light. In one embodiment, the tissue sample is washed to remove excess, unbound conjugate, and fluorescence of the tissue sample is assessed. Fluorescence indicates that the conjugate has bound to the tissue sample.

Embodiments of conjugate precursors according to Formula I, IA, or IB wherein $R^c$ comprises a succinimidyl, maleimidyl, or dibenzocyclooctynyl group are suitable for customized conjugation to a targeting agent of choice. In one non-limiting example, a tumor sample is obtained from a subject. An antibody that specifically recognizes and binds to an antigen on the tumor, or a ligand that specifically recognizes and binds to a receptor on the tumor, is prepared by methods known to one of ordinary skill in the art. The prepared antibody or ligand is then reacted with $R^c$ of the selected conjugate precursor to provide a customized conjugate suitable for administration to the subject.

Conjugate precursors according to Formula I, IA, or IB are suitable for customized conjugation to a selected targeting agent. In one embodiment, the conjugate precursor is used by a pharmaceutical company to develop a conjugate having a desired targeting agent. In another embodiment, the conjugate precursor is used by a researcher or clinician to develop conjugates having desired targeting agents useful for research purposes or for developing a customized conjugate for treating a subject.

VII. KITS

Kits are also a feature of this disclosure. Embodiments of the kits include at least one conjugate or a conjugate precursor as disclosed herein. In one embodiment, the kit includes a conjugate wherein $R^c$ comprises a targeting agent, e.g., an antibody or a ligand. In another embodiment, the kit includes conjugate precursor wherein $R^c$ comprises

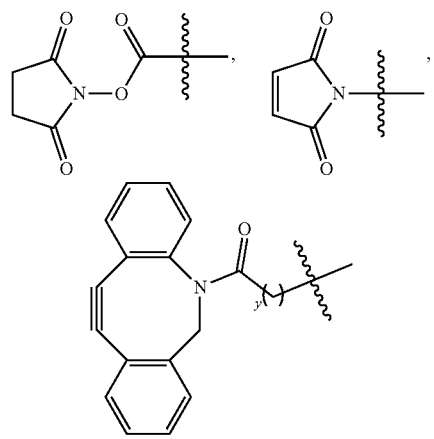

where y is an integer≥1, or —OH, and the kit may be used to prepare a conjugate comprising a desired targeting agent, wherein the targeting agent is capable of reacting with the conjugate precursor to provide a conjugate comprising the targeting agent. In some examples, the conjugate precursor is FNIR-Tag.

In some embodiments, the kits also include at least one solution in which the conjugate or conjugate precursor may be dissolved or suspended. The kits also may include one or more containers, such as a disposable test tube or cuvette. The kits may further include instructions for using a conjugate according to Formula I, IA, IB, II, IIA, or IIB, and/or for preparing a conjugate comprising a desired targeting agent from a conjugate precursor according to Formula I, IA, or IB. In some embodiments, the kits further include reagents suitable for conjugating the conjugate precursor to a targeting agent.

In some embodiments of the kits, the conjugate or conjugate precursor is provided as a solid, and the solution is provided in liquid form. In one embodiment, the solution is suitable for dissolving a conjugate according to Formula I, IA, IB, II, IIA, or IIB so that the dissolved conjugate may be administered to a subject. In an independent embodiment, the solution is suitable for dissolving a conjugate precursor according to Formula I, IA, or IB for subsequent conjugation to a targeting agent. The solution may be provided at a concentration suitable for the intended use. Alternatively, the solution may be provided as a concentrated solution, which is subsequently diluted prior to use. In certain embodiments, the conjugate or conjugate precursor is premeasured into one or more containers (e.g., vials, syringes, test tubes, or cuvettes).

VIII. HEPTAMETHINE CYANINES FOR USE AS FLUORESCENT MARKERS

Representative embodiments of heptamethine cyanines for use a fluorescent markers are described in the following numbered clauses.

1. A compound, or a stereoisomer thereof, according to Formula III:

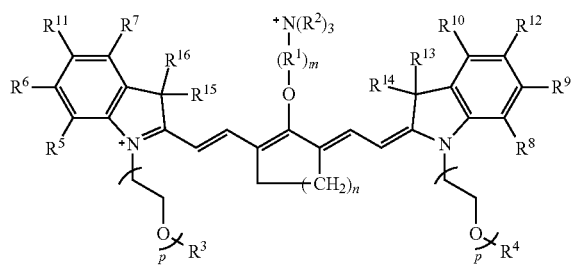

(III)

wherein m is 3, 4, or 5; n is 1, 2, or 3; each p independently is 1, 2, 3, 4, 5, 6, 7, 8, 9, or 10; $R^1$ is —$CR^a_2$— where each $R^a$ independently is H, halo, optionally substituted alkyl, or optionally substituted aryl; each $R^2$ independently is methyl, ethyl, n-propyl, or isopropyl; $R^3$ and $R^4$ independently are alkyl; $R^5$ to $R^{10}$ independently are H or alkyl; $R^{11}$ and $R^{12}$ independently are sulfonate, H, or alkyl; and $R^{13}$ to $R^{16}$ independently are alkyl.

2. The compound of clause 1, wherein: $R^3$ and $R^4$ are the same; $R^5$ and $R^8$ are the same; $R^6$ and $R^9$ are the same; $R^7$ and $R^{10}$ are the same; $R^{11}$ and $R^{12}$ are the same; and $R^{13}$-$R^{16}$ are the same.

3. The compound of clause 1 or clause 2, wherein p is 2, 3, or 4.

4. The compound of clause 1, according to Formula IIIA:

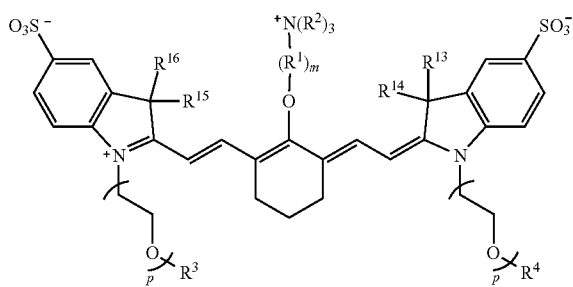

(IIIA)

wherein $R^1$ is —$CH_2$—; m is 3; and p is 2, 3, or 4.

5. The compound of any one of clauses 1-4, wherein: (i) $R^3$ and $R^4$ are methyl; (ii) $R^{13}$-$R^{16}$ are methyl; or (iii) both (i) and (ii).

6. A compound, or a stereoisomer thereof, according to Formula IV:

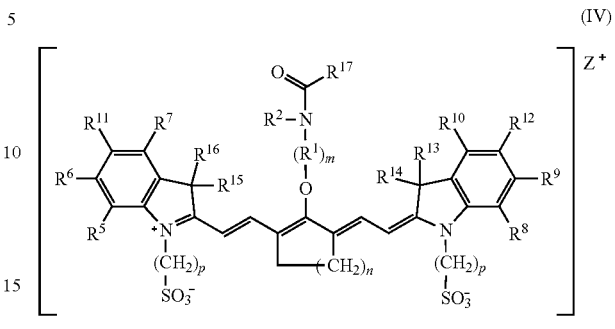

(IV)

wherein m is 2, 3, 4, or 5; n is 1, 2, or 3; each p independently is 1, 2, 3, 4, 5, 6, 7, 8, 9, or 10; $R^1$ is —$CR^a_2$— where each $R^a$ independently is H, halo, optionally substituted alkyl, or optionally substituted aryl; $R^2$ is $C_1$-$C_3$ alkyl; $R^5$ to $R^{12}$ independently are H or alkyl; $R^{13}$ to $R^{16}$ independently are alkyl; $R^{17}$ is $C_1$-$C_3$ alkyl; and Z is a monatomic ion.

7. The compound of clause 6, wherein: $R^5$ and $R^8$ are the same; $R^6$ and $R^9$ are the same; $R^7$ and $R^{10}$ are the same; $R^{11}$ and $R^{12}$ are the same; and $R^{13}$-$R^{16}$ are the same.

8. The compound of clause 6 or clause 7, wherein p is 3, 4, or 5.

9. The compound of clause 6, according to Formula IVA:

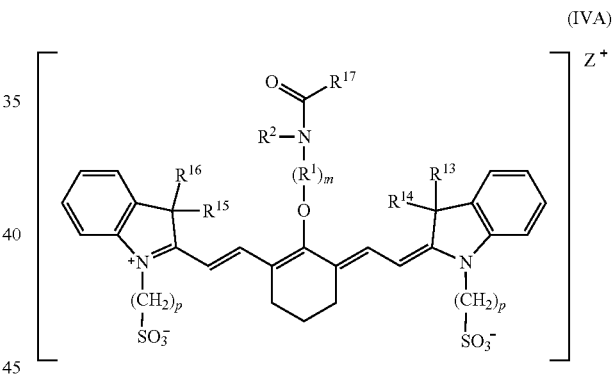

(IVA)

wherein $R^1$ is —$CH_2$—; m is 2; and p is 3, 4, or 5.

10. The compound of any one of clauses 6-9, wherein: (i) $R^{17}$ is methyl or ethyl; (ii) $R^{13}$ to $R^{16}$ are methyl; or (iii) both (i) and (ii).

11. The compound of any one of clauses 1-10, wherein each $R^2$ independently is methyl or ethyl.

12. The compound of clause 1, wherein the compound is:

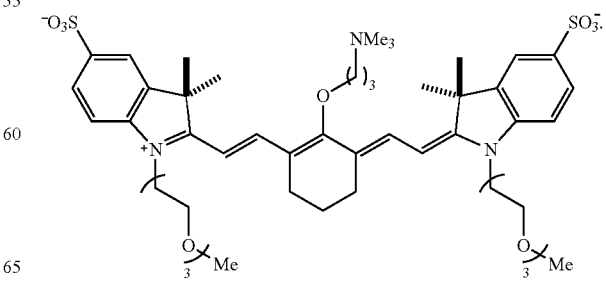

13. The compound of clause 6, wherein the compound is:

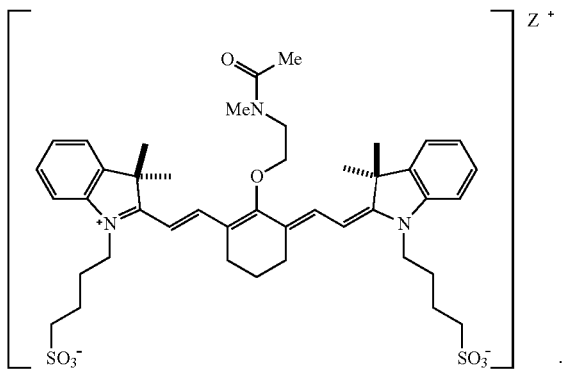

14. A pharmaceutical composition, comprising: a compound according to any one of clauses 1-13; and a pharmaceutically acceptable carrier.

IX. EXAMPLES

General Materials and Methods. Unless stated otherwise, reactions were conducted in oven-dried glassware under an atmosphere of nitrogen or argon using anhydrous solvents (passed through activated alumina columns). All commercially obtained reagents were used as received. N-[(3-(anilinomethylene)-2-chloro-1-cyclohexen-1-yl)methylene] aniline monohydrochloride XX were purchased from Sigma-Aldrich (St. Louis, Mo.), IRDye®-800CW-COOH dye and IRDye®-800CW-NHS dye were purchased from LI-COR (Lincoln, Nebr.). Flash column chromatography was performed using reversed phase (100 Å, 20-40 micron particle size, RediSep® Rf Gold® Reversed-phase C18 or C18Aq) and silica on a CombiFlash® Rf 200i (Teledyne Isco, Inc.). High-resolution LC/MS analyses were conducted on a Thermo-Fisher LTQ-Orbitrap-XL hybrid mass spectrometer system with an Ion MAX API electrospray ion source in negative ion mode. Analytical LC/MS was performed using a Shimadzu LCMS-2020 Single Quadrupole utilizing a Kinetex 2.6 μm C18 100 Å (2.1×50 mm) column obtained from Phenomenex, Inc. Runs employed a gradient of 0→90% MeCN/0.1% aqueous formic acid over 4.5 mM at a flow rate of 0.2 mL/min $^1$H NMR and $^{13}$C NMR spectra were recorded on Bruker spectrometers (at 400 or 500 MHz or at 100 or 125 MHz) and are reported relative to deuterated solvent signals. Data for $^1$H NMR spectra are reported as follows: chemical shift (δ ppm), multiplicity, coupling constant (Hz), and integration. Data for $^{13}$C NMR spectra are reported in terms of chemical shift. IR spectra were recorded on a Jasco FT/IR-4100 spectrometer and are reported in terms of frequency of absorption (cm$^{-1}$). Absorption curves for quantum yield measurements were performed on a Shimadzu UV-2550 spectrophotometer operated by UVProbe 2.32 software. Fluorescence traces were recorded on a PTI QuantaMaster steady-state spectrofluorimeter operated by FelixGX 4.2.2 software, with 5 nm excitation and emission slit widths, 0.1 s integration rate, and enabled emission correction. Data analysis and curve fitting were performed using MS Excel 2011 and GraphPad Prism 7. Light intensity measurements were performed with a Thorlabs PM200 optical power and energy meter fitted with an S120VC standard Si photodiode power sensor (200-1100 nm, 50 nW 50 mW). Flow cytometry was performed at the CCR Flow Cytometry Core (NCI-Frederick) and microscopy was performed at the Optical Microscopy and Analysis Laboratory (NCI-Frederick). See *JOC Standard Abbreviations and Acronyms* for abbreviations (http://pubs.acs.org/userimages/ContentEditor/1218717864819/joceah_abbreviations.pdf).

Determination of Molar Absorption Coefficients and Absolute Fluorescence Quantum Yields: Molar absorption coefficients (c) were determined in PBS (pH 7.4) or 1:1 (v/v) MeOH/PBS (pH 7.4) using Beer's law, from plots of absorbance vs. concentration. Measurements were performed in 10 mm path length quartz cuvettes (Hellma 111-QS), maintained at 25° C., with absorbance at the highest concentration≤0.20.

Absolute quantum yields ($\Phi_F$) were measured using a Quantaurus-QY spectrometer (Hamamatsu, model C11374). This instrument is equipped with an integrating sphere to determine photons absorbed and emitted by a sample. Measurements were carried out at a concentration of 500 nM in PBS (50 mM, pH 7.4) and self-absorption corrections were performed using the instrument software.

Cell Culture: MDA-MB-468 (EGFR overexpression) human breast cancer cell line was obtained from NCI DTP, DCTD Tumor Repository. The cells were cultured in DMEM supplemented with 2 mM L-glutamine, 11 mM D-glucose, 24 mM sodium bicarbonate, 10% heat-inactivated fetal bovine serum, 100 units/mL penicillin, 100 μg/mL streptomycin, and 0.25 μg/mL amphotericin B. The cells were grown at 37° C. in an atmosphere of 20% $O_2$ and 5% $CO_2$, and were passaged following trypsinization with 0.25% Trypsin-EDTA in PBS. The cells were evaluated for molecular testing of biological materials by animal health diagnostic laboratory at Frederick National Laboratory for Cancer Research. The results confirmed the absence of the following agents within the cells: Ectromelia virus (ECT), Mouse rotavirus (EDIM), Lymphocytic coriomeningitis virus (LCMV), Lactic dehydrogenase elevating virus (LDHV), Mouse adenovirus (MAD), Mouse cytomegalovirus (MCMV), Mouse hepatitus virus (MHV), Mouse norovirus (MNV), Mouse parvovirus (MPV), Minute virus of mice (MVM), *Mycoplasma* spp. (MYCO), Polyoma virus (POLY), Pneumonia virus of mice (PVM), Reovirus 3 (REO3), Sendai virus (SEN), Theiler's murine encephalomyelitis virus (TMEV).

Animal Tumors Models: In vivo studies were performed according to the Frederick National Laboratory for Cancer Research (Frederick, Md.) Animal Care and Use committee guidelines. Fluorescence was longitudinally monitored employing the IVIS spectrum imager (PerkinElmer Inc, Waltham, Mass.). Imager specific Living Image software was used for image acquisition and analysis. Mice body temperature were maintained constant at 37° C. during the imaging procedure with a heated pad located under the anesthesia induction chamber, imaging table, and post procedure recovery cage. All mice were anesthetized in the induction chamber with 3% isoflurane with filtered (0.2 μm) air at 1 liter/minute flow rate for 3-4 minutes and then modified for imaging to 2% with $O_2$ as a carrier with a flow rate of 1 liter/minute. Static 2D images were acquired with the following parameters: excitation filter 745±15 nm, emission filter 800±10 nm, f/stop2, medium binning (8×8) and auto exposure (typically 1-60 seconds). 5-week old female athymic nude mice were purchased from Charles River Laboratories International, Inc. (NCI-Frederick). MDA-MB-468 (5×10$^6$) in 100 μL of Hanks Balanced Salt Solution were injected the mice subcutaneously in the right dorsum.

The size of the tumors were continuously monitored to reach 4-6 mm. In vivo studies were initiated 10 days post cell injection of the mice.

Data Analysis: Images were obtained using a Pearl Imager (LI-COR) using 800 nm fluorescence channel. Using white light images, the tumors were identified, and regions of interest (ROIs) were located on the tumors, livers, and necks (used as background). The intensities of ROIs were measured based on the total radiance efficiency using fluorescence images and analyzed using Living Image software. Statistics (unpaired t-test) were carried out using Prism 8.

Example 1

Heptamethine Cyanine Synthesis and Characterization

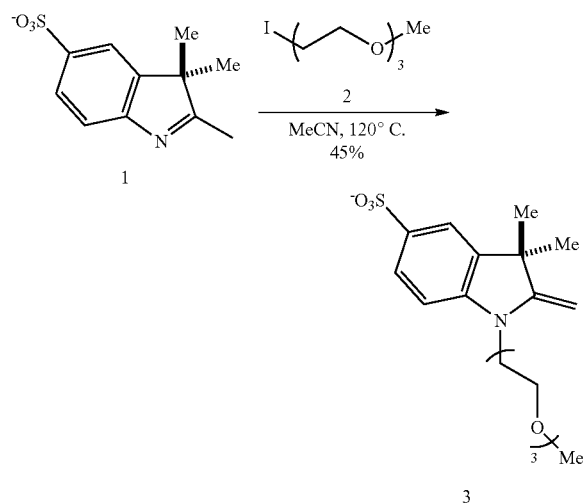

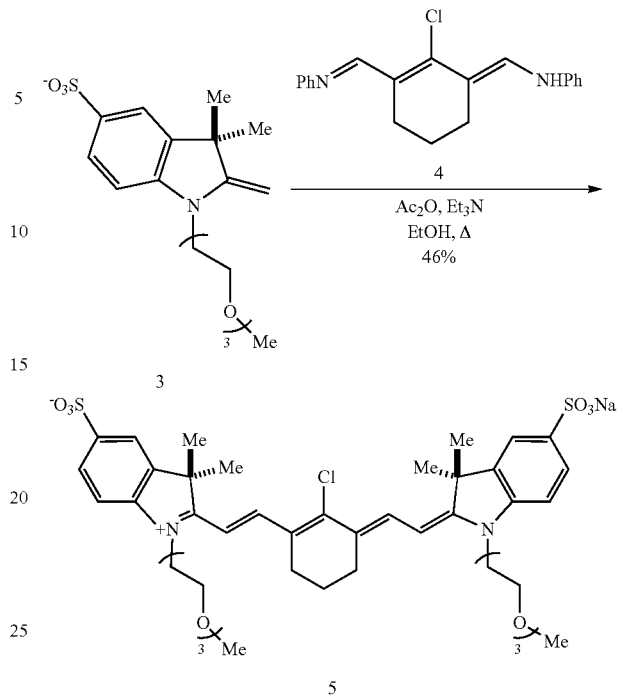

(3): To a microwave vial equipped with a magnetic stir bar was added indolenine 1 (3.0 g, 10.8 mmol; Park et al., Bioconjugate Chem. 2012, 23:350), MeCN (12 mL) and iodide 2 (3.0 g, 10.8 mmol; Lawal et al., Supramol. Chem. 2009, 21:55). The vessel was sealed under argon and the light brown slurry was heated to 120° C. in a sand bath for 22 hours during which time the reaction changed to a deep red/pink color. The reaction was cooled and the solvent removed by rotary evaporation. Water (10 mL) was added to the red crude and purified by reversed-phase chromatography ($C_{18}$ Aq, 0→30% MeCN/water). The product-containing fractions were combined and the solvent removed by rotary evaporation to afford 3 (2.1 g, 45% yield) as a red gummy solid. $^1$H NMR (400 MHz, DMSO-$d_6$ exists as 93:7 ratio of enamineimine tautomers) δ 7.38-7.29 (m, 2H), 6.59 (d, J=8.0 Hz, 1H), 3.96 (d, J=1.9 Hz, 1H), 3.88 (d, J=1.9 Hz, 1H), 3.68 (t, J=6.0 Hz, 2H), 3.57 (t, J=6.0 Hz, 2H), 3.52-3.43 (m, 6H), 3.41-3.36 (m, 2H), 3.22 (s, 3H), 1.26 (s, 6H); $^{13}$C NMR (125 MHz, DMSO-$d_6$) δ 160.6, 145.7, 139.3, 135.7, 125.3, 119.4, 104.2, 74.7, 71.2, 70.1, 69.8, 69.6, 66.4, 58.0, 43.5, 41.9, 29.7; IR (thin film) 2921, 1715, 1650, 1604, 1486, 1382, 1182 cm$^{-1}$; HRMS (ESI) calculated for $C_{18}H_{28}NO_6S$ (M+H)$^+$ 386.1632, observed 386.1632.

(5, Chloride 1): To a microwave tube equipped with a magnetic stir bar was added indolenine 3 (2.07 g, 4.9 mmol) in ethanol (14 mL) and chloride 4 (0.45 g, 1.4 mmol). The vessel was sealed and flushed with argon. Triethylamine (1.37 mL, 9.8 mmol), and acetic anhydride (1.85 mL, 19.6 mmol) were then added in succession by syringe. The yellow solution was heated to 120° C. for 30 minutes, during which time the reaction transitioned to a deep green color. The reaction was cooled and the solvent removed by rotary evaporation. Saturated aqueous $NaHCO_3$ (17 mL) was added and the green residue was purified by reversed-phase chromatography ($C_{18}$, 0→30% MeCN/water). The product-containing fractions were lyophilized to afford 5 (1.04 g, 46% yield) as a green solid. $^1$H NMR (500 MHz, methanol-$d_4$) δ 8.46 (d, J=14.1 Hz, 2H), 7.92 (d, J=1.7 Hz, 2H), 7.88 (dd, J=8.3, 1.7 Hz, 2H), 7.40 (d, J=8.4 Hz, 2H), 6.49 (d, J=14.1 Hz, 2H), 4.41 (t, J=5.1 Hz, 4H), 3.91 (t, J=5.1 Hz, 4H), 3.60-3.57 (m, 4H), 3.53-3.50 (m, 4H), 3.48-3.44 (m, 4H), 3.41-3.37 (m, 4H), 3.28 (s, 6H), 2.75 (t, J=6.2 Hz, 4H), 2.00-1.91 (m, 2H), 1.77 (s, 12H); $^{13}$C NMR (125 MHz, methanol-$d_4$) δ 175.6, 151.4, 145.7, 145.3, 143.6, 142.4, 129.0, 128.0, 121.3, 112.4, 104.2, 72.9, 72.1, 71.7, 71.4, 69.2, 59.1, 50.7, 46.1, 28.3, 27.4, 22.1; IR (thin film) 2864, 1546, 1509, 1427, 1387, 1234, 1151 cm$^{-1}$; HRMS (ESI) calculated for $C_{44}H_{60}ClN_2O_{12}S_2$ (M+H)$^+$ 907.3271, observed 907.3268.

Example 2

Conjugate Precursor Synthesis and Characterization

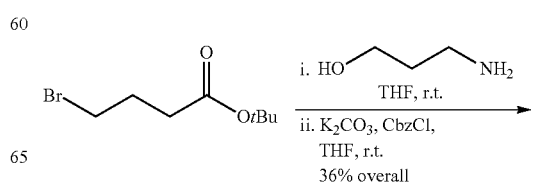

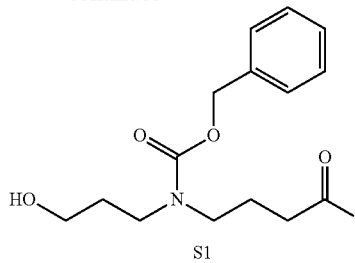

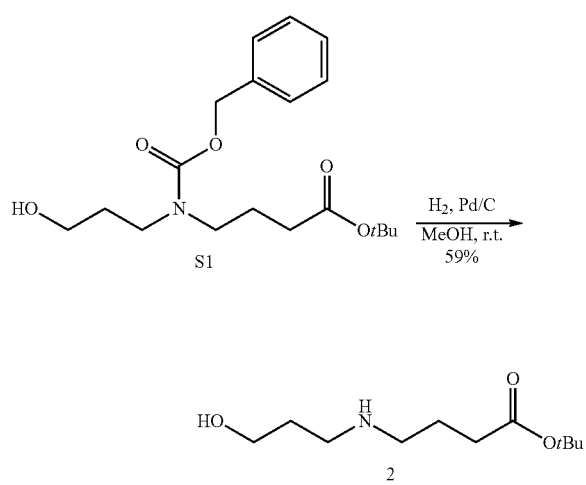

To a 20 mL microwave tube equipped with a magnetic stir bar was added tert-butyl 4-bromobutyrate (4.84 g, 21.9 mmol), 3-aminopropanol (10.0 mL, 131.6 mmol, 6 equiv.) and dry THF (5.0 mL) under argon. The reaction was stirred at room temperature for 2 h, at which time LC-MS analysis indicated consumption of the starting material. The biphasic reaction mixture was diluted with brine (100 mL) and extracted with $CH_2Cl_2$ (3×100 mL). The organic layers were combined, dried over $MgSO_4$, and concentrated by rotary evaporation to afford the crude mixture of alkylated products. To the crude oil (3.81 g) in a 100 mL round bottom flask equipped with a stir bar and septum was added dry THF (17 mL), $K_2CO_3$ (2.72 g, 19.7 mmol, 1.1 equiv.) and flushed with argon. Cbz-Cl (7.6 mL, 53.7 mmol, 3 equiv.) in THF (3.0 mL) was added dropwise under argon and the reaction mixture was stirred at room temperature for 0.5 h. The yellow suspension was then concentrated by rotary evaporation and partitioned between water (50 mL) and $CH_2Cl_2$ (50 mL) The layers were separated, and the aqueous layer was extracted once more with $CH_2Cl_2$ (50 mL). The organic layers were combined, washed with water and brine, then dried over $MgSO_4$. The clear solution was concentrated by rotary evaporation and purified by column chromatography (40 g silica, 0→60% EtOAc/Hexane) to afford the Cbz-protected linker S1 as a yellow oil in 36% yield (2.73 g): $^1$H NMR (400 MHz, $CD_3CN$) δ 7.37 (d, J=4.4 Hz, 4H), 7.32 (m, 1H), 5.09 (s, 2H), 3.46 (t, J=5.9 Hz, 2H), 3.32 (t, J=7.0 Hz, 2H), 3.25 (t, J=7.3 Hz, 2H), 2.17 (t, 2H), 1.76 (p, J=7.3 Hz, 2H), 1.67 (p, J=6.6 Hz, 2H), 1.41 (s, 9H) ppm; $^{13}$C NMR (100 MHz, $CDCl_3$) δ 172.34, 157.56, 136.65, 128.66, 128.21, 127.99, 80.61, 67.58, 58.46, 46.26, 43.39, 32.73, 30.60, 28.20, 23.97 ppm; HRMS (ESI) calculated for $C_{19}H_{30}NO_5$ (M+H)$^-$ 352.2118, observed 352.2108.

Cbz deprotection (2): To a microwave tube equipped with a magnetic stir bar was added Pd/C (10 wt %, 273 mg), then sealed and flushed with argon. S1 (2.73 g, 7.8 mmol) dissolved in MeOH (20 mL, 0.4 M) was added under argon. The reaction mixture was evacuated and backfilled with a $H_2$ balloon 4×, then stirred under $H_2$ atmosphere for 1 h, at which time LC-MS analysis indicated complete consumption of S1. The reaction mixture was filtered through celite and concentrated to afford 2 as a clear oil in 59% yield (993 mg) that solidified on standing: $^1$H NMR (500 MHz, Chloroform-d) δ 3.78 (t, J=5.3 Hz, 2H), 2.85 (t, J=5.7 Hz, 2H), 2.61 (t, J=7.1 Hz, 2H), 2.24 (t, J=7.4 Hz, 2H), 1.74 (p, J=7.3 Hz, 2H), 1.70-1.63 (m, 2H), 1.42 (s, 9H). $^{13}$C NMR (125 MHz, Chloroform-d) δ 172.7, 80.2, 64.3, 49.9, 49.0, 33.2, 30.7, 28.0, 25.2; IR (thin film) 3410, 1725, 1500, 1322, 1254 cm$^{-1}$; HRMS (ESI) calculated for $C_{11}H_{23}NO_3$ (M+H)$^-$ 218.1751, observed 218.1742.

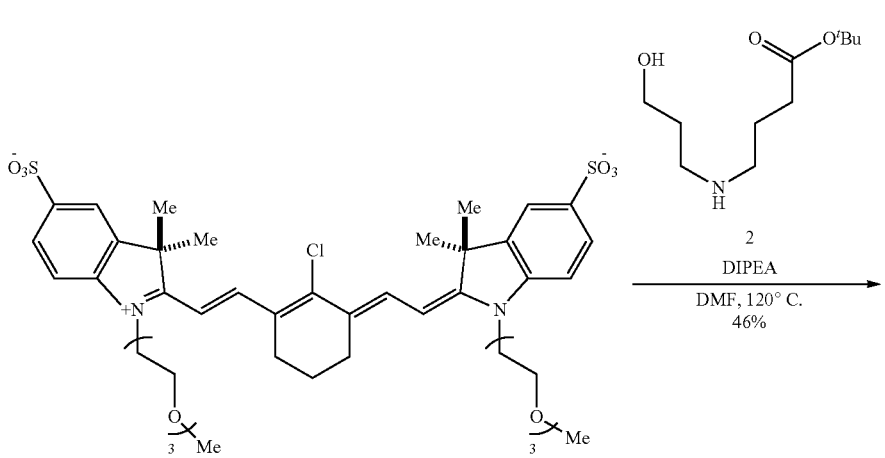

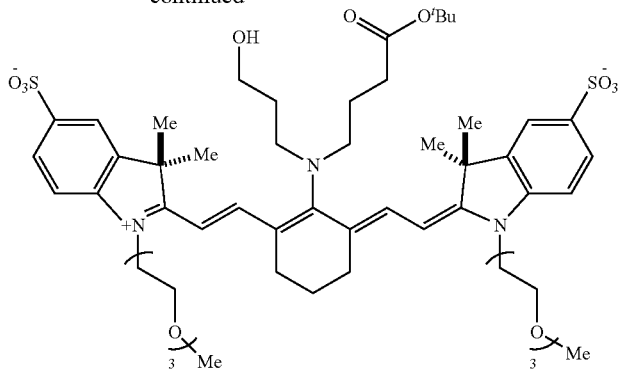

3

(3): To a microwave vial was added chloride 1 (compound 5 of Example 1) (91 mg, 0.17 mmol) and DMF (0.5 mL). tert-Butyl 4-((3-hydroxypropyl)amino)butanoate, 2, (267 mg, 1.2 mmol) and DIPEA (92 µL, 0.53 mmol) were added and the solution was sparged with argon for 2 minutes. The reaction was heated to 120° C. for 25 minutes, during which time the reaction color transitioned from green to dark blue. The reaction was cooled and diluted with saturated aqueous NaHCO$_3$ (4 mL) and the solution was directly purified by reversed-phase chromatography (C$_{18}$ Aq gold, 0→40% MeCN/water). The product-containing fractions were lyophilized to afford 3 (91 mg, 47% yield) as blue solid. $^1$H NMR (400 MHz, DMSO-d$_6$) δ 7.71-7.48 (m, 6H), 7.19 (d, J=8.3 Hz, 2H), 6.09 (d, J=13.6 Hz, 2H), 4.56 (t, J=4.8 Hz, 1H), 4.30-4.17 (m, 4H), 3.80-3.58 (m, 8H), 3.53-3.46 (m, 6H), 3.46-3.37 (m, 12H), 3.17 (s, 6H), 2.47-2.44 (m, 4H), 2.25 (t, J=7.0 Hz, 2H), 1.94-1.84 (m, 2H), 1.86-1.78 (m, 2H), 1.77-1.69 (m, 2H), 1.58 (s, 12H), 1.42-1.34 (m, 2H), 1.34 (s, 9H); $^{13}$C NMR (100 MHz, DMSO-d$_6$) δ 173.0, 171.4, 169.7, 144.0, 142.9, 141.5, 139.3, 125.9, 124.6, 119.4, 109.5, 97.6, 79.8, 71.2, 70.3, 69.8, 69.7, 67.4, 58.1, 58.0, 54.4, 52.6, 47.6, 43.7, 32.1, 31.9, 28.5, 27.7, 24.5, 24.2, 21.6; IR (thin film) 3413, 2927, 2869, 1722, 1507, 1364, 1254, 1155 cm$^{-1}$; HRMS (ESI) calculated for C$_{55}$H$_{82}$N$_3$O$_{15}$S$_2$ (M+H)$^-$ 1088.5182, observed 1088.5139.

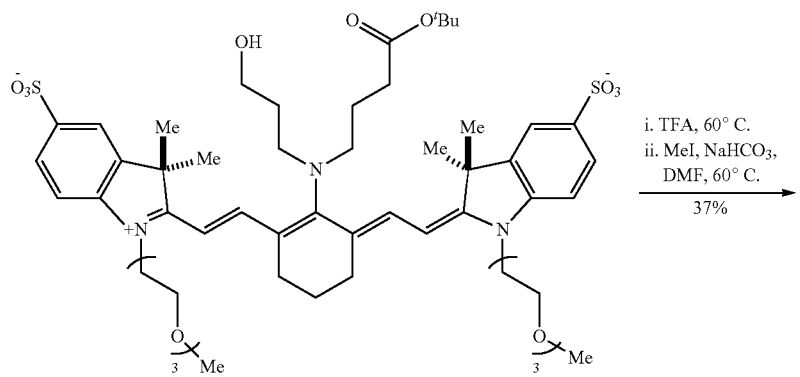

3

-continued

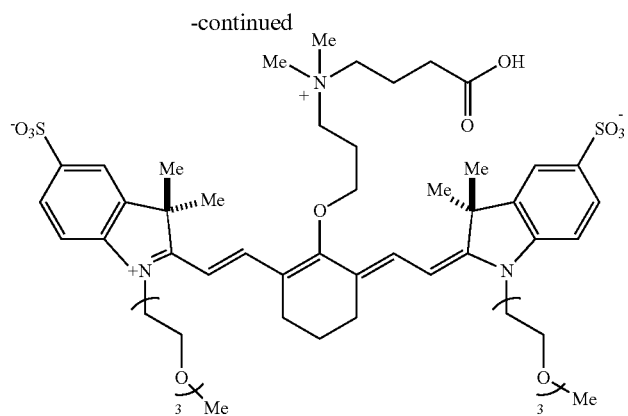

4

(4): To a round bottom flask was added cyanine 3 (341 mg, 0.31 mmol) and TFA (4.0 mL). The red solution was heated to 60° C. for 5 minutes under argon. The TFA was removed in vacuo and the residue was placed under vacuum (<0.1 Torr) for 5 minutes. DMF (8.0 mL), NaHCO$_3$ (1.37 g) and methyl iodide (1.0 μL) were added and the reaction was heated to 60° C. for 4 hours. The reaction was cooled and diluted with water and the solution was directly purified by reversed-phase chromatography (C$_{18}$ Aq gold, 0→40% MeCN/water). The product-containing fractions were lyophilized to afford 4 (110 mg, 33% yield) and 5 (100 mg, 30% yield) as green solids. $^1$H NMR (500 MHz, DMSO-d$_6$) δ 7.94 (d, J=13.9 Hz, 2H), 7.81 (d, J=1.7 Hz, 2H), 7.63 (dd, J=8.3, 1.6 Hz, 2H), 7.33 (d, J=8.4 Hz, 2H), 6.28 (d, J=14.2 Hz, 2H), 4.44-4.30 (m, 4H), 4.08-3.97 (m, 2H), 3.79 (t, J=5.1 Hz, 4H), 3.71-3.62 (m, 2H), 3.53-3.47 (m, 4H), 3.43-3.37 (m, 8H), 3.34-3.27 (m, 4H), 3.23 (s, 6H), 3.18 (s, 6H), 2.63-2.53 (m, 1H), 2.42-2.32 (m, 4H), 2.06-1.93 (m, 2H), 1.86-1.75 (m, 2H), 1.69 (s, 12H); $^{13}$C NMR (125 MHz, DMSO-d$_6$) δ 173.6, 172.2, 168.5, 145.2, 142.4, 140.1, 139.5, 126.0, 122.3, 119.7, 110.6, 100.8, 73.5, 71.2, 70.3, 69.8, 69.7, 67.5, 62.2, 60.2, 58.0, 50.7, 48.6, 44.2, 30.8, 27.8, 23.9, 23.8, 20.7, 18.0; IR (thin film) 2874, 1721, 1557, 1506, 1392, 1360, 1248, 1151 cm$^{-1}$; HRMS (ESI) calculated for C$_{53}$H$_{79}$N$_3$O$_3$S$_2$ (M+2H)$^{2+}$ 530.7471, observed 530.7447.

Saponification of 5. (182 mg, 0.169 mmol) was dissolved in 1:1 MeOH:H$_2$O in a scintillation vial equipped with a magnetic stir bar and pierceable septum. The green solution was cooled to 0° C., and 1M NaOH (540 μL, 40 equiv.) was added dropwise. The reaction mixture was allowed to stir and warm to r.t (2 h), as the color gradually turned yellow. The reaction mixture was then quenched with formic acid (1.3 mL), followed by addition of water (5.0 mL) and saturated aqueous NaHCO$_3$ (10 mL). The green solution was directly purified by reversed-phase column chromatography (C$_{18}$ Aq gold, 10→30% MeCN/water) to afford 4 as a green solid in 56% yield (98 mg).

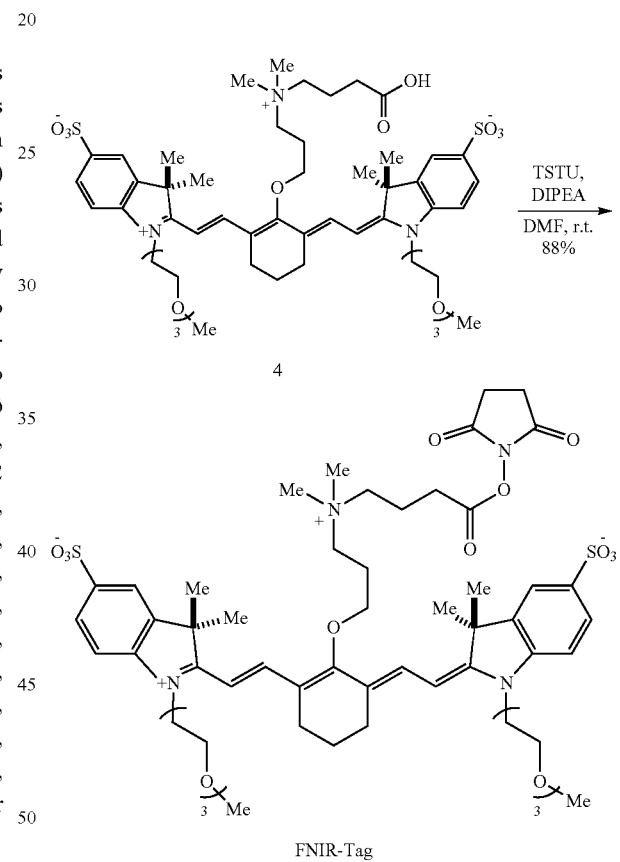

(FNIR-tag): To a 1 dram vial was added cyanine 4 (2.2 mg, 0.0021 mmol) and DMF (0.5 mL). DIPEA (0.7 μL, 0.004 mmol) and TSTU (1.2 mg, 0.004 mmol) were added in succession. After 30 minutes at room temperature complete conversion to the NHS ester was observed by LC/MS. The reaction was inversely added to diethyl ether (2 mL) resulting in a green precipitate. After centrifugation the solid was placed under vacuum (<0.1 Torr) for 1 hour, yielding FNIR-Tag (2.1 mg, 88% yield) as green solid. HRMS (ESI) calculated for C$_{57}$H$_{82}$N$_4$O$_{17}$S$_2$ (M+2H)$^{2+}$ 579.2555, observed 579.2525.

Properties of FNIR-Tag and IRDye®-800CW are shown below in Table 1. As expected, the C4' O-alkyl cyanine exhibits an absorption/emission maxima (765/788 nm) well in the NIR region that is similar to IR-800CW, 774/795 nm. Both dyes have similar absorption coefficients (ε), absolute quantum yields ($\Phi_F$) and brightness (ε×$\Phi_F$) in PBS solution, with free IR-800CW being slightly brighter

TABLE 1

|  | IRDye®-800CW | FNIR-Tag |
|---|---|---|
| $\lambda_{abs}$ (nm) | 774 | 765 |
| $\lambda_{em}$ (nm) | 795[a] | 788[b] |
| ε ($M^{-1} \cdot cm^{-1}$) | 240 000 | 200 000 |
| $\Phi_F$ (PBS) | 0.087 | 0.099 |
| ε × $\Phi_F$ | 23 490 | 19 800 |
| Relative brightness (PBS) | 1.2 | 1.0 |

[a]$\lambda_{excitation}$ = 740 nm, [b]$\lambda_{excitation}$ = 730 nm

Figure 3A:
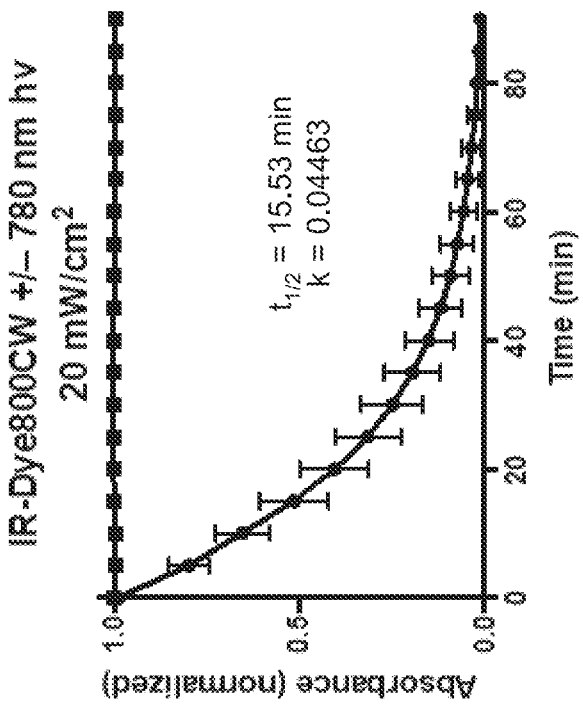
FIGS. 3A and 3B show photooxidation kinetics of a conjugate precursor (FNIR-Tag) as disclosed herein (3A) and a commercial dye IRDye®-800CW dye (3B) where the free dyes are indicated with circles and dark controls are indicated with squares.
Figure 3B:
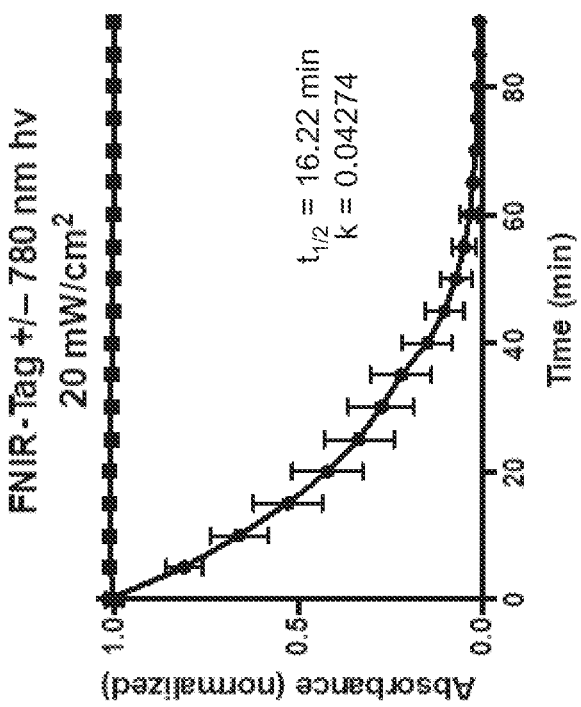

Stock solutions of 5 mM FNIR-Tag and IRDye®-800CW in DMSO were diluted into 50 mM PBS (pH=7.4) to afford 1 μM solutions. The photostability was determined using a procedure described previously using a 780 nm+/−20 nm LED at a light intensity of 20 mW/cm² (Nani et al., *ACS Central Sci* 2017, 3:329). FIGS. 3A and 3B show that FNIR-Tag exhibits $t_{1/2}$ of 16.22 min with k=0.04274 (3A), and IRDye®-800CW exhibits $t_{1/2}$ of 15.53 mM with k=0.04463 (3B). As expected both of the free dyes have similar photostability.

Example 3

Conjugation of FNIR-Tag with Panitumumab

Figure 4A:
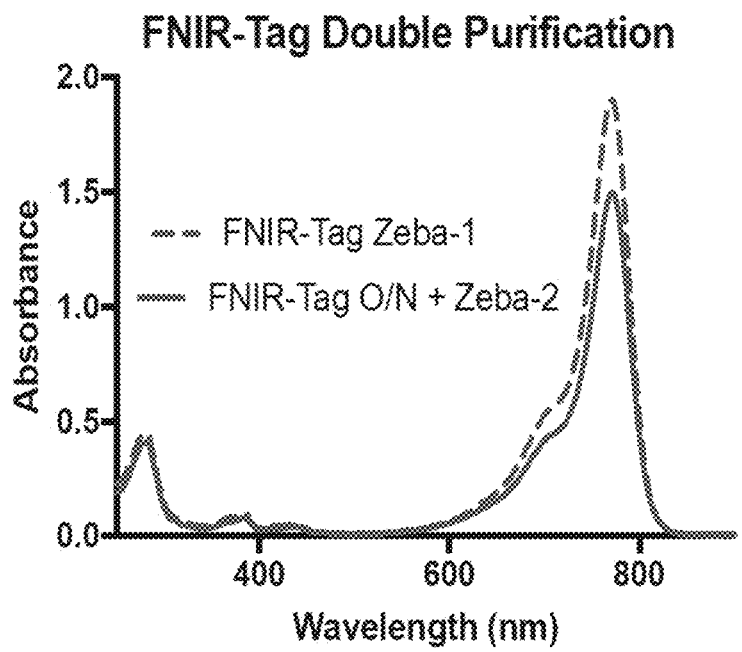
FIGS. 4A and 4B are absorbance spectra of FNIR-Tag-panitumumab (4A) and IRDye®-800CW-panitumumab (4B) conjugates.
Figure 4B:
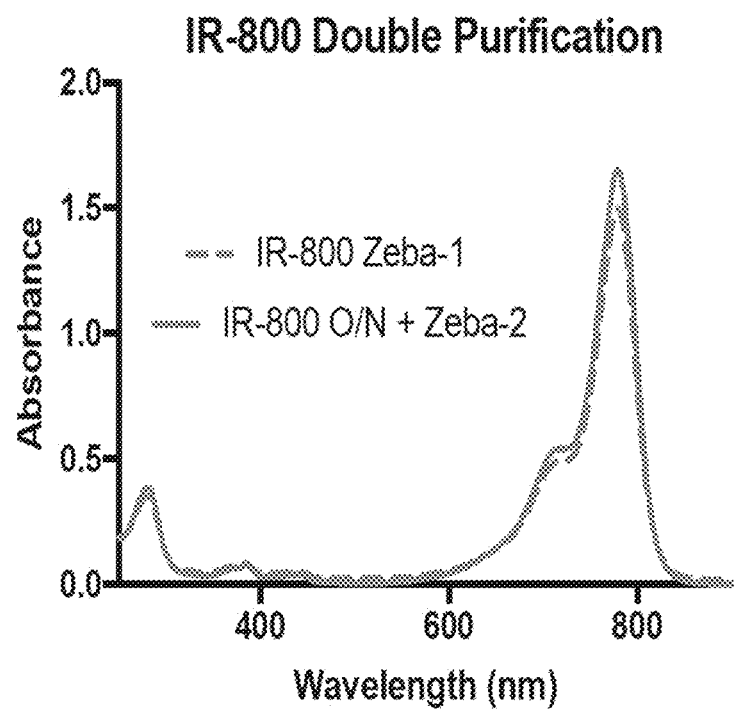

Conjugation of FNIR-Tag with the anti-EGFR mAb Panitumumab was carried out in 50 mM PBS (pH 7.4) with molar excesses of 2.2, 4.4 and 8.1 to provide the desired lysine-labeled panitumumab conjugates with degree of labeling (DOL) of 1, 2 and 4 (±0.2), respectively. All steps were performed under reduced lighting. To 100 μL of 50 mM PBS (pH 7.4) in a 1.5 mL microcentrifuge tube was added 200 μL of Panitumumab (20 mg/mL commercial stock solution). In a separate 1.5 mL microcentrifuge tube, a 10 mM DMSO stock solution of IRDye®-800CW-NHS (1.5, 2.9, 6.1 eq. for DOL 1, 2 and 4 respectively) or FNIR-Tag (2.2, 4.4, 8.1 eq. for DOL 1, 2 and 4 respectively) was quickly premixed with 100 μL PBS and immediately transferred to the panitumumab solution. The resulting mixture was gently pipetted and inverted and incubated at room temperature for 1 h. The solution was eluted through a pH 7.4 PBS equilibrated Zeba spin DS column (7K MWCO, Thermo Fisher Scientific) to remove unreacted free dye. To remove nonspecifically bound dye from the protein, conjugate solutions were incubated at 25° C. in the dark for 18 h, and repurified by size exclusion chromatography using a Zeba spin DS column (FIGS. 4A-4B), which led to a moderate decrease in labeling. Notably, labeling proceeded with greater efficiency at pH 7.4 then at pH 8.5, even though the more basic pH is conventionally used for NHS-ester labeling studies. This observation may be attributed to the enhanced chemical reactivity of FNIR-Tag NHS-ester, which perhaps arises from the strong inductive effect of the electron withdrawing quaternary amine Labeled samples with IRDye®-800CW conjugates (DOL 1, 2, and 4) were obtained by carrying out the labeling using 1M PBS (pH 8.5).

Figure 5:
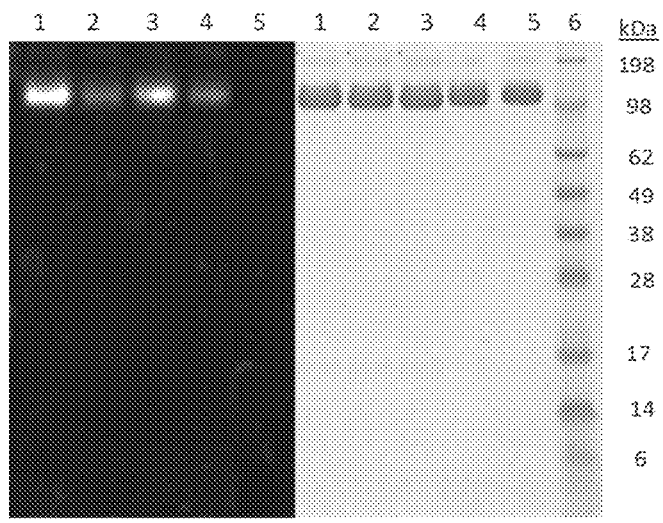
FIG. 5 shows SDS-PAGE analysis of panitumumab labeled with (1) FNIR-Tag (degree of labeling (DOL) 4), (2) IRDye®-800CW dye (DOL 4), (3) FNIR-Tag (DOL2), and (4) IRDye®-800CW (DOL 2).

Sodium dodecyl sulfate-polyacrylamide gel electrophoresis (SDS-PAGE) was performed to confirm the presence of covalent bonding of dyes to antibody. 5 μg of each conjugated antibody were loaded on NuPAGE® 4-12% Bis-Tris gels (ThermoFisher Scientific) under non-reductive conditions in 1×MES SDS buffer at 200 V for 35 mM with 1:4 (v/v) solution of NuPAGE® LDS sample buffer and 50 mM PBS, pH 7.4. SeeBlue® Plus2 Prestained Protein Standard (ThermoFisher Scientific) was used for molecular weight comparison. Fluorescence images were obtained using an ImageQuant® LAS 4000 (GE Healthcare) camera system with Cy5 excitation. Exposure time was 50 seconds. White images were collected using trans-illumination (1 second exposure time), and analyzed using ImageJ. FIG. 5 shows the results of panitumumab labeled with (1) FNIR-Tag (DOL 4), (2) IRDye®-800CW dye (DOL 4), (3) FNIR-Tag (DOL 2), and (4) IRDye®-800CW (DOL 2).

Figure 6A:
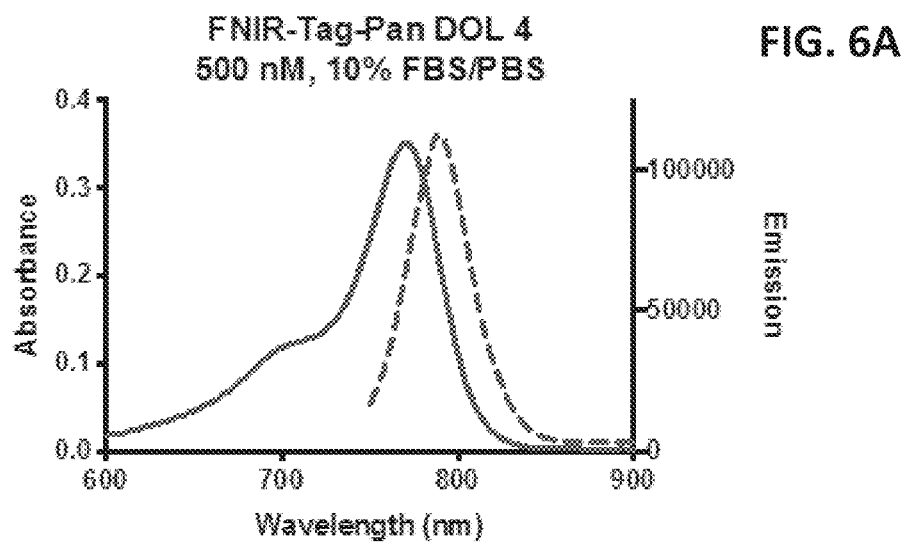
FIGS. 6A and 6B show absorption (solid lines) and emission (dashed lines) spectra of FNIR-Tag-panitumumab DOL 4 (6A) and IRDye®-800CW-panitumumab DOL 4 (6B) in 10% fetal bovine serum/phosphate-buffered saline solution at a protein concentration of 500 nM.
Figure 6B:
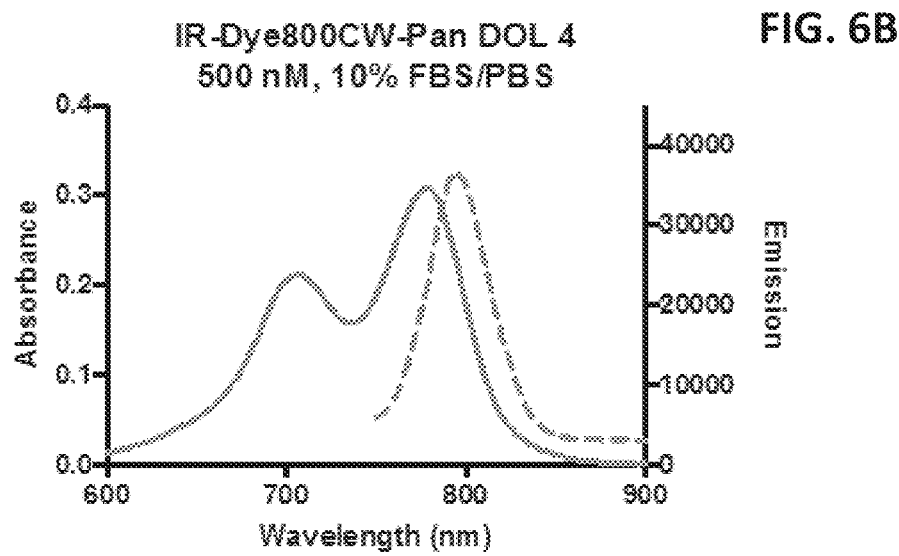
Figure 7A:
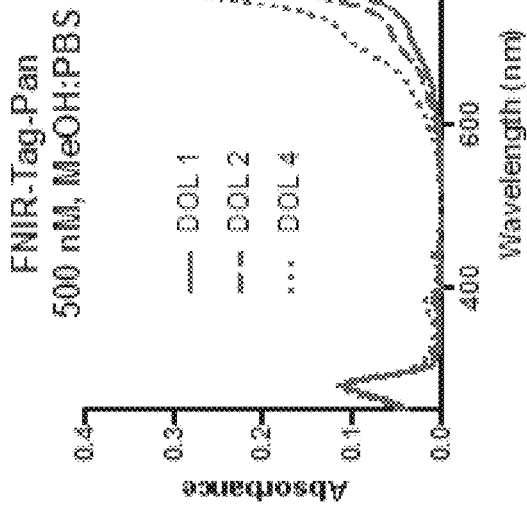
FIGS. 7A and 7B show absorption spectra of FNIR-Tag-panitumumab conjugates at DOL 1, 2, and 4 (500 nM) in PBS (7A) and 50:50 MeOH:PBS (7B).
Figure 7B:
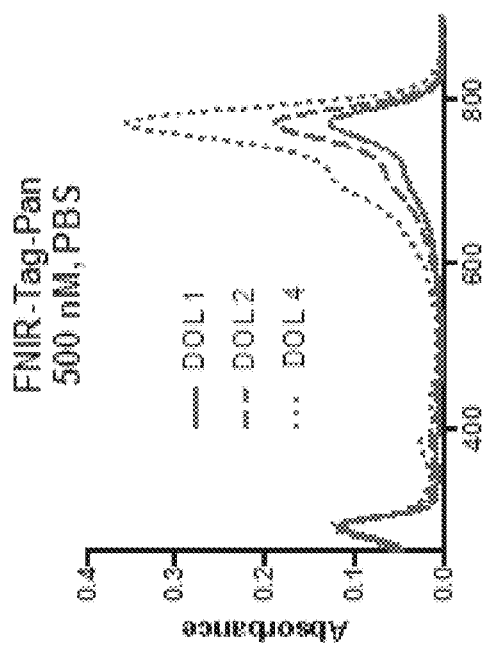
Figure 8A:
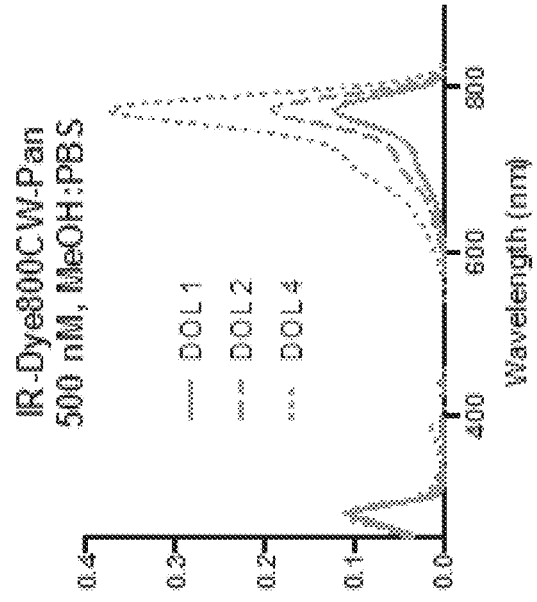
FIGS. 8A and 8B show absorption spectra of IRDye®-800CW-panitumumab conjugates at DOL 1, 2, and 4 (500 nM) in PBS (8A) and 50:50 MeOH:PBS (8B).
Figure 8B:
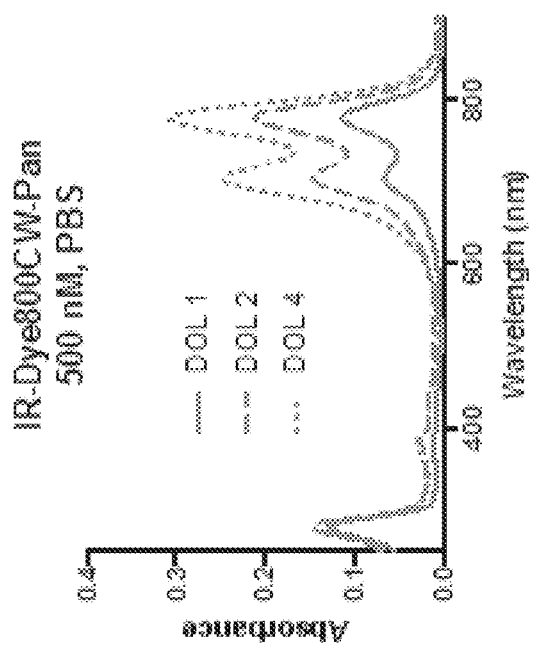
Figure 9A:
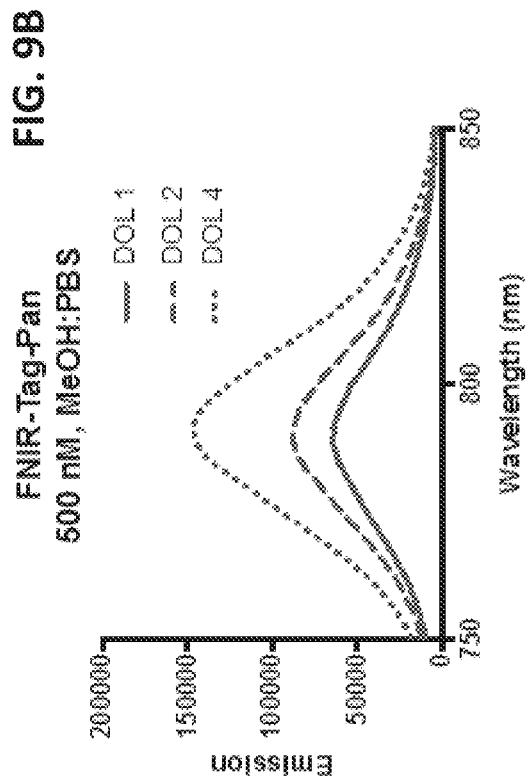
FIGS. 9A and 9B show emission spectra of FNIR-Tag-panitumumab conjugates at DOL 1, 2, and 4 (500 nM) in PBS (9A) and 50:50 MeOH:PBS (9B).
Figure 9B:
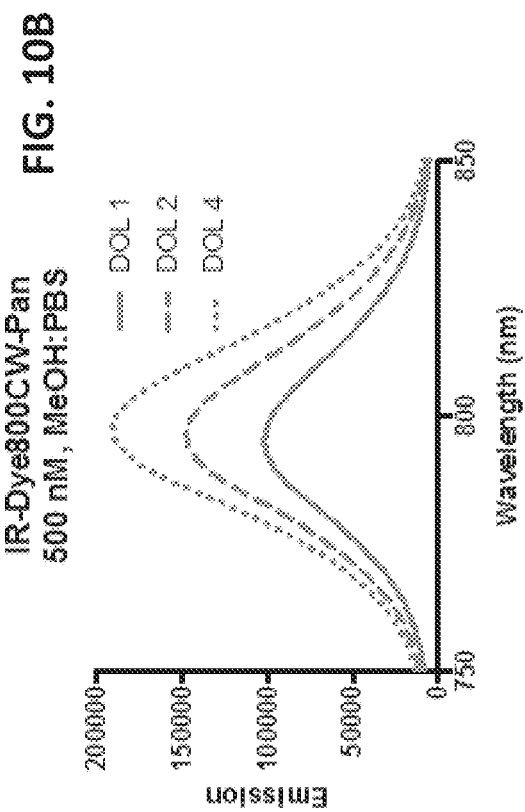
Figure 10A:
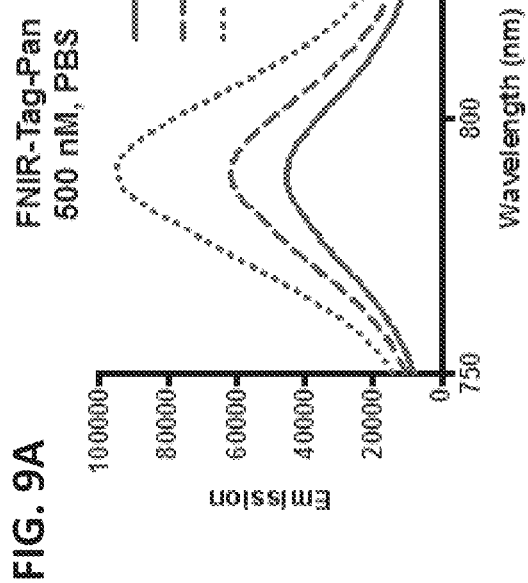
FIGS. 10A and 10B show emission spectra of IRDye®-800CW-panitumumab conjugates at DOL 1, 2, and 4 (500 nM) in PBS (10A) and 50:50 MeOH:PBS (10B).
Figure 10B:
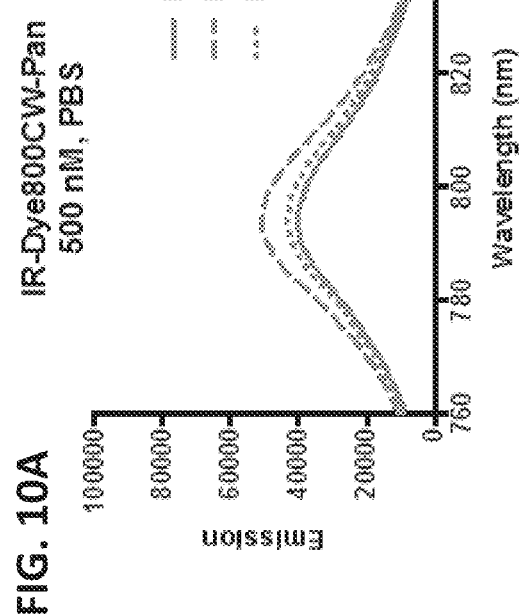
Figure 11:
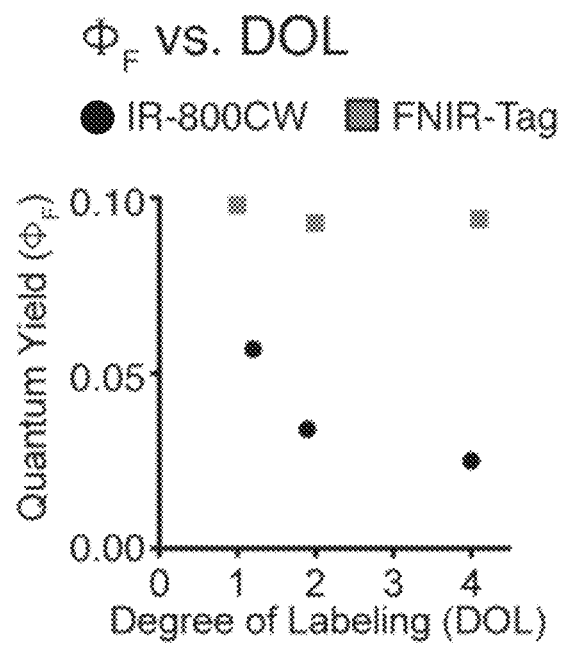
FIG. 11 shows absolute quantum yields of fluorescence of the conjugates of FIGS. 7-10 (250 nM effective dye concentration) in PBS.

The photochemical properties of these conjugates were analyzed by several methods. Absorption/emission curves were obtained following dilution in 50 mM PBS to yield solutions that were 500 nM in protein concentration. FIGS. 6A and 6B show absorption (solid lines) and emission (dashed lines) spectra of FNIR-Tag-panitumumab DOL 4 (6A) and IRDye®-800CW-panitumumab DOL 4 (6B) in 10% fetal bovine serum (FBS)/phosphate-buffered saline (PBS) solution at a protein concentration of 500 nM. A 3 h incubation time at room temperature elapsed prior to acquisition. Conjugates were diluted 40-fold into 1:1 MeOH:50 mM PBS and their absorption spectra were recorded on a plate reader using a 384 well plate transparent in the 280 nm range (i.e. UV Co-Star μclear 384 well plate from Greiner Bio-One). FIGS. 7A and 7B show absorption spectra of FNIR-Tag-panitumumab conjugates at DOL 1, 2, and 4 (500 nM) in PBS (7A) and 50:50 MeOH:PBS (7B). FIGS. 8A and 8B show absorption spectra of IRDye®-800CW-panitumumab conjugates at DOL 1, 2, and 4 (500 nM) in PBS (8A) and 50:50 MeOH:PBS (8B) ($\lambda_{excitation}$=730 nm). FIGS. 9A and 9B show emission spectra of FNIR-Tag-panitumumab conjugates at DOL 1, 2, and 4 (500 nM) in PBS (9A) and 50:50 MeOH:PBS (9B). FIGS. 10A and 10B show emission spectra of IRDye®-800CW-panitumumab conjugates at DOL 1, 2, and 4 (500 nM) in PBS (10A) and 50:50 MeOH:PBS (10B) ($\lambda_{excitation}$=740 nm). FIG. 11 shows absolute quantum yields of fluorescence of the conjugates (250 nM effective dye concentration) in PBS.

The formation of a significant H-aggregate peak in the absorption spectrum (~705 nm) is apparent with the IRDye®-800CW conjugates even at DOL 1, which worsens at higher DOL of 2 and 4 (FIG. 8A). By contrast, FNIR-Tag does not form a significant H-aggregate band throughout over this range of labeling density (FIG. 7A). Of note, this trend persists in the presence of serum proteins (FIGS. 6A-6B).

The impact of H-aggregation on the fluorescent emission of these conjugates is dramatic. With IRDye®-800CW, the fluorescent emission of the antibody conjugates in PBS is nearly constant across the range of labeling density, meaning added fluorophores do not increased brightness of the individual antibody conjugates (FIG. 10A). By contrast, the emission of FNIR-Tag-panitumumab conjugates increases with higher labeling density (FIG. 9A). Demonstrating that this effect is the result of H-aggregation, diluting the IRDye®-800CW conjugates in 50:50 MeOH:PBS to denature the protein removes the presence of H-aggregate peak and increase the emission of the conjugates (FIGS. 8B, 10B).

Figure 12:
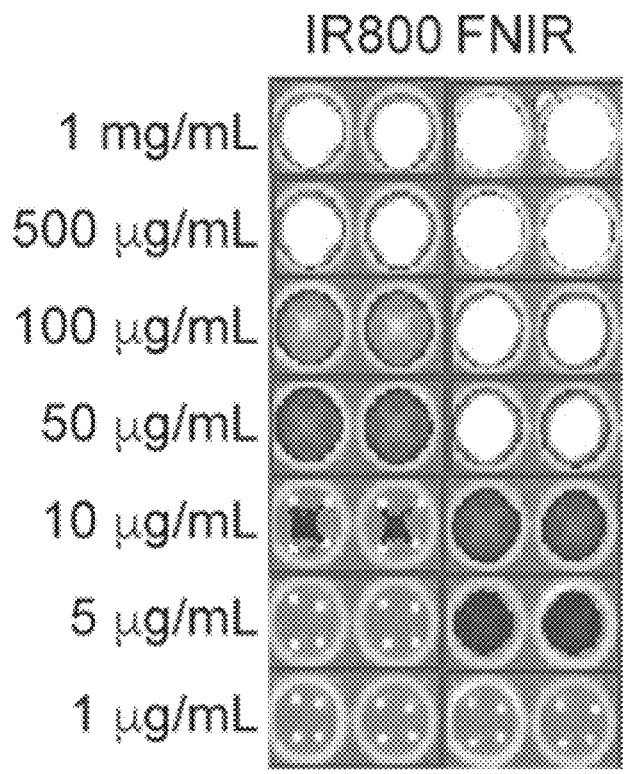
FIG. 12 shows Phantom IVIS® system in vivo imaging of DOL4-panitumumab conjugates with FNIR-Tag and IRDye®-800CW in 50 mM pH 7.4 PBS.

The impact of aggregation on emissive properties of these conjugates can also be seen by measuring the absolute quantum yields of fluorescence ($\Phi_F$) of these differentially labeled conjugates (FIG. 11). In the case of IR-800CW-antibody conjugates, quantum yield decreased as a function of increased labeling from ~9% to ~2.5%. By contrast, the quantum yield of FNIR-Tag conjugates nearly maintained the value of the free dye (10%) with increasing labeling density. To examine the relative brightness of these conjugates on an in vivo system, phantom imaging on the Perkin-Elmer IVIS® imaging system was performed. FIG. 12 shows the in vivo imaging of DOL4-panitumumab conjugates in 50 mM pH 7.4 PBS. DOL-4 antibody conjugates of FNIR-Tag could readily visualized at a lower concentration (0.5 μg/mL) than required for similarly labeled conjugates of IR-Dye® 800CW (1 to 5 μg/mL).

Example 4

Biodistribution of FNIR-Tag-Panitumumab Conjugate in Mice

Figure 13:
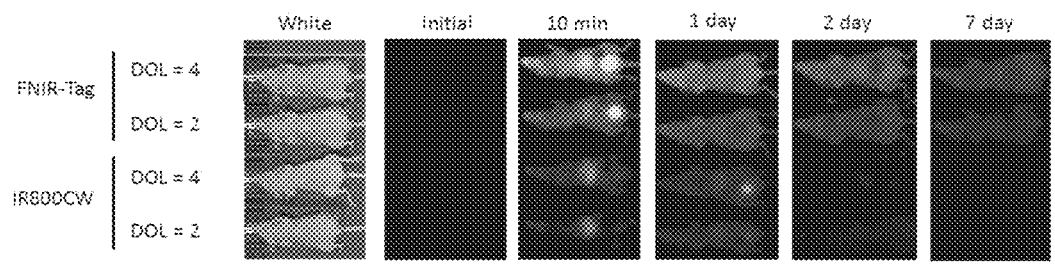
FIG. 13 shows ventral fluorescence images of mice treated with 100 μg of IRDye®-800CW and FNIR-Tag panitumuab conjugates (DOL 2 and 4) by tail injection.
Figure 14:
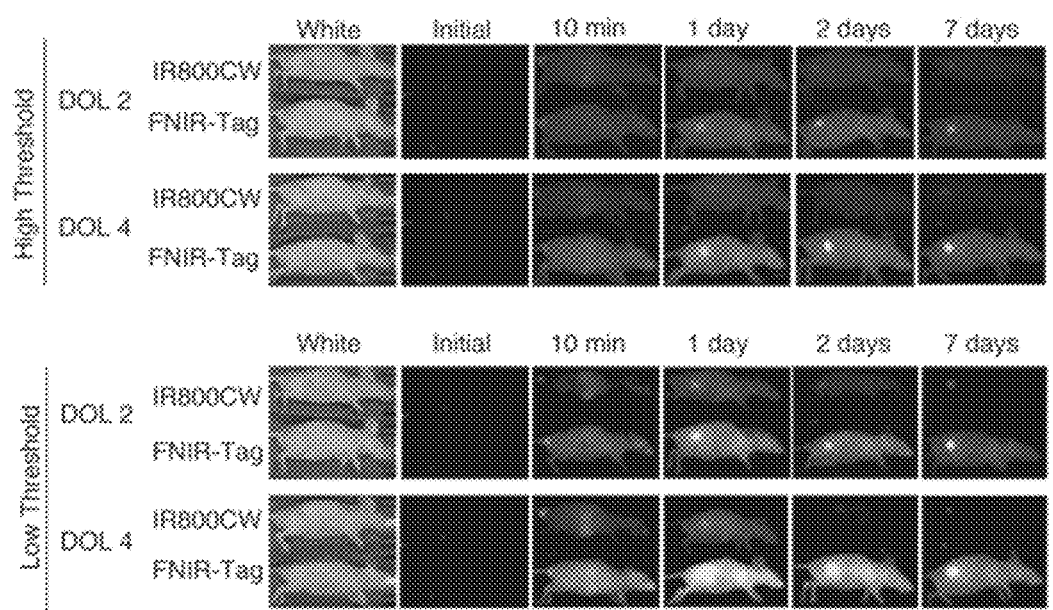
FIG. 14 shows dorsal fluorescence images of mice treated with 100 μg of IRDye®-800CW and FNIR-Tag panitumuab conjugates (DOL 2 and 4) by tail injection.

The data above suggested that FNIR-Tag might have favorable fluorescence properties relative to IR-800CW in vivo. Reduced dye aggregation was speculated to impact the pharmacokinetics. To compare the brightness of the two conjugates, in vivo imaging was carried out using athymic nude mice bearing EGFR+ tumors implanted in their right flank (n=5 per group). The mice were injected in the tail with 100 μg of either IRDye®-800CW or FNIR-Tag conjugates of panitumumab at DOL 2 or 4. Fluorescence dorsal and ventral images were recorded at 0 h, 10 min, 24 h, 48 h, and 1 week post-injection. IRDye®-800CWVentral and dorsal fluorescence images are shown in FIGS. 13 and 14.

Figure 15:
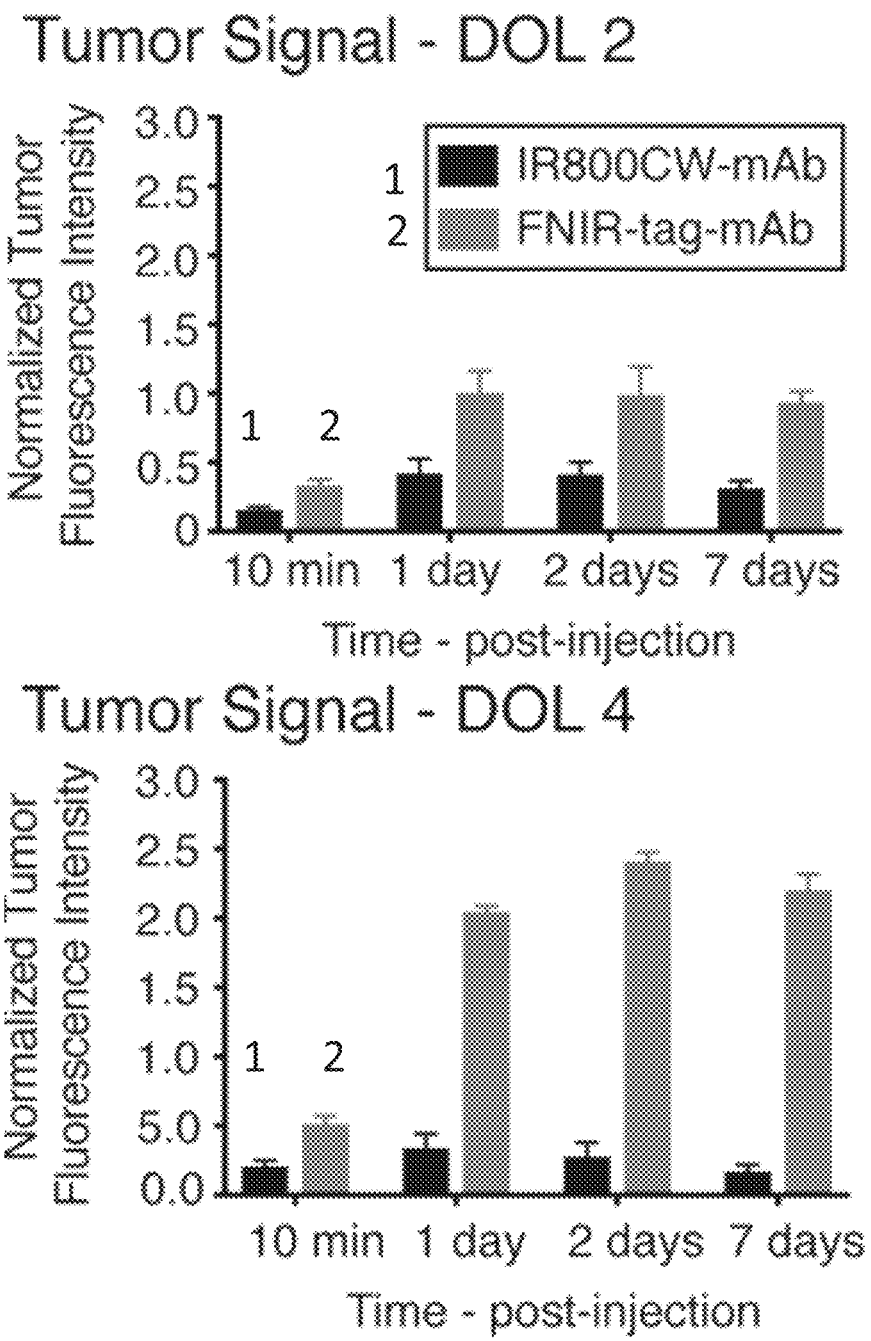
FIG. 15 shows tumor signal (total radiance, all values×$10^{10}$) normalized to tumor size for DOL 2 (upper panel) and DOL 4 (lower panel).
Figure 16:
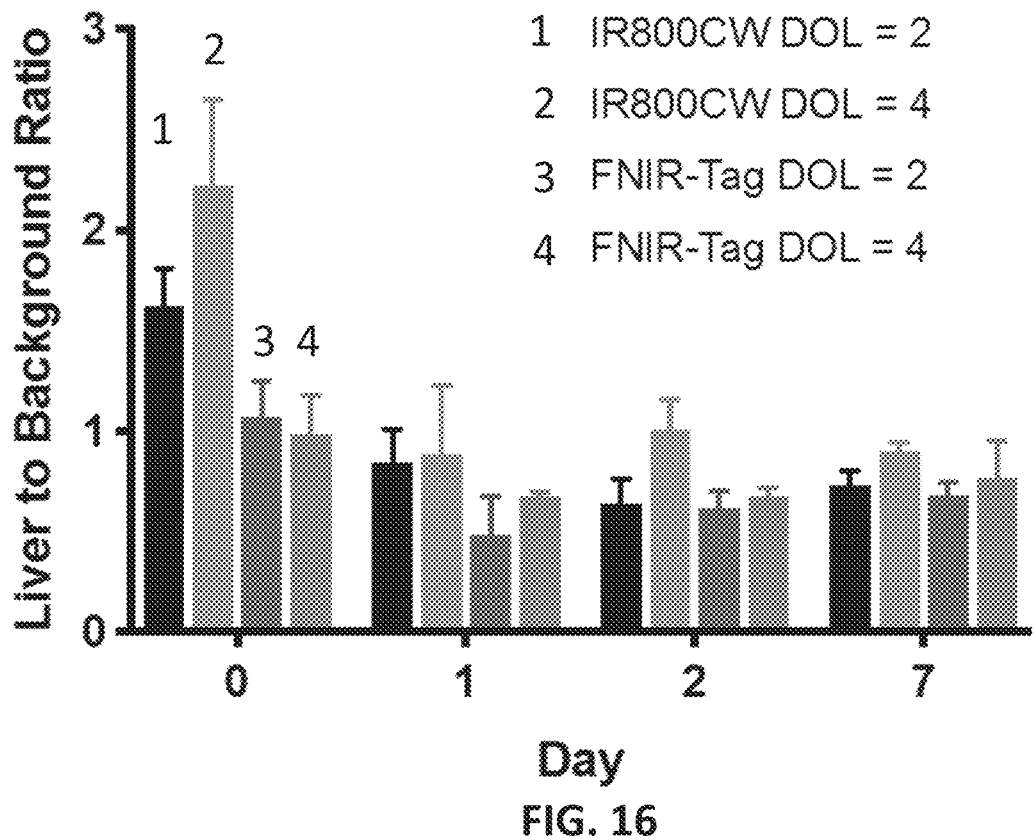
FIG. 16 is a graph quantifying the liver-to-background ratio of ventral images of mice treated with 100 μg of IRDye®-800CW and FNIR-Tag conjugates (DOL 2 and 4) by tail vein injection.
Figure 17:
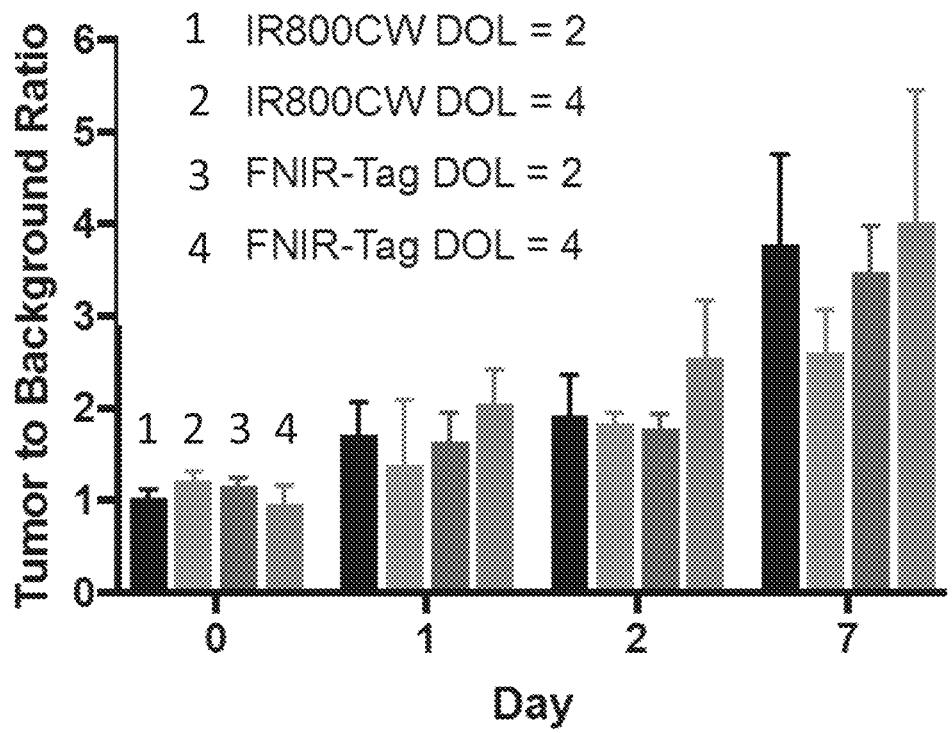
FIG. 17 is a graph quantifying the tumor to background ratio of dorsal images of mice treated with 100 μg of IRDye®-800CW and FNIR-Tag conjugates (DOL 2 and 4) by tail vein injection.

FIG. 15 shows tumor signal (total radiance, all values× $10^{10}$) normalized to tumor size for DOL 2 (upper panel) and DOL 4 (lower panel). All paired columns are statistically different (p<0.001). At the peak accumulation of both fluorophores in the tumor (48 h), the radiance output of FNIR-Tag was 2.5× higher at DOL 2 and 7.1× higher at DOL 4. At an initial 10 min time point there was significantly higher liver uptake of the IRDye®-800CW than with FNIR-Tag conjugates (FIG. 16). However, at the 100 μg dose the tumor to background (TBR, taken in the neck region) ratio was indistinguishable through this time course (FIG. 17). The latter observation is perhaps not surprising, as this dose was previously optimized for IRDye®-800CW conjugates and not for conjugates of this new brighter dye.

Figure 18:
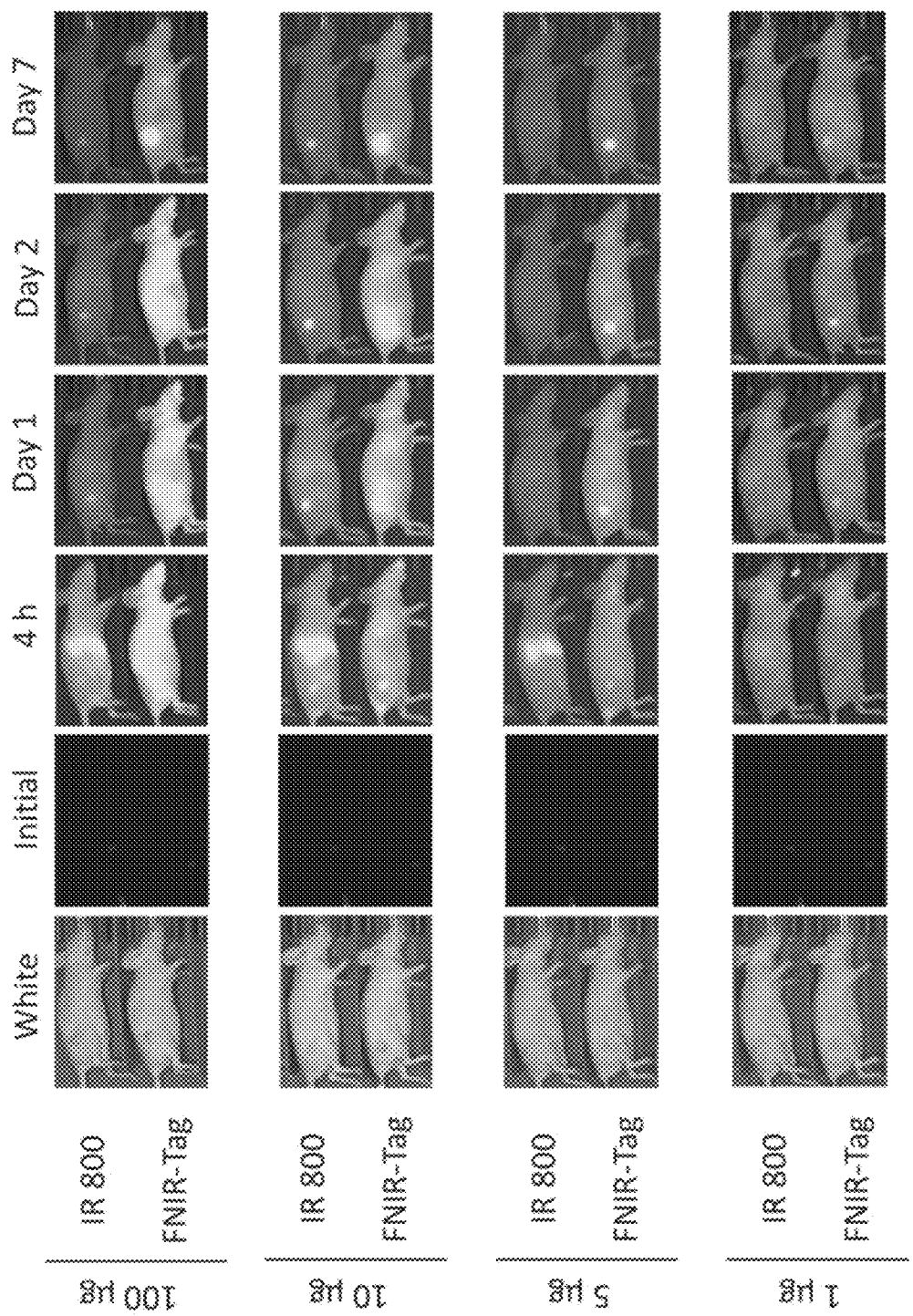
FIG. 18 shows dorsal fluorescence images of MDA-MB-468 tumor-bearing mice injected with 100 μg, 10 μg, 5 μg, and 1 μg of DOL 4 IRDye®-800CW and FNIR-Tag pre-injection and 4 hours, 1 day, 2 days and 7 days timepoints post-injection.
Figure 19:
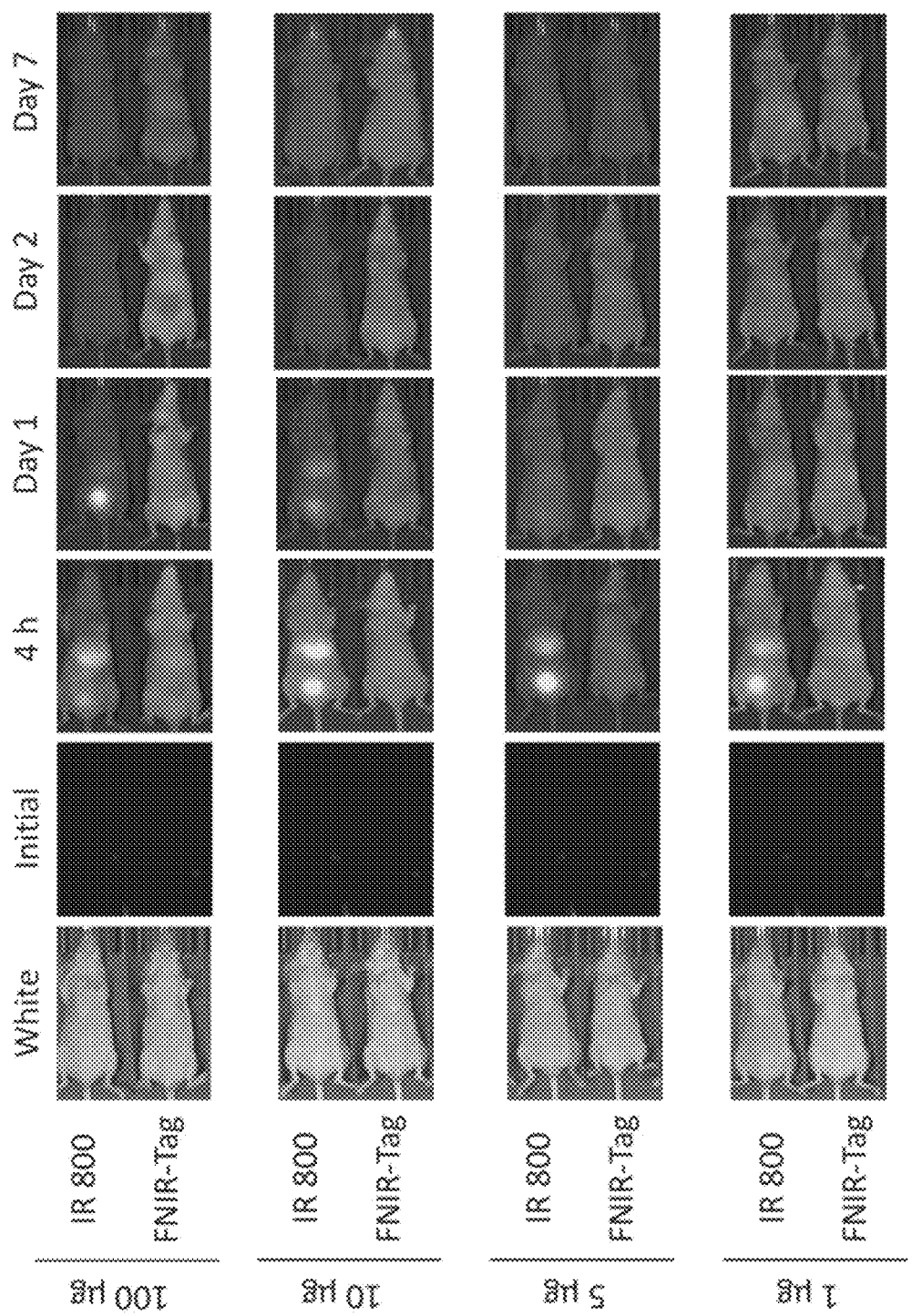
FIG. 19 shows ventral fluorescence images of MDA-MB-468 tumor-bearing mice injected with 100 μg, 10 μg, 5 μg, and 1 μg of DOL 4 IRDye®-800CW and FNIR-Tag pre-injection and 4 hours, 1 day, 2 days and 7 days timepoints post-injection.
Figure 20:
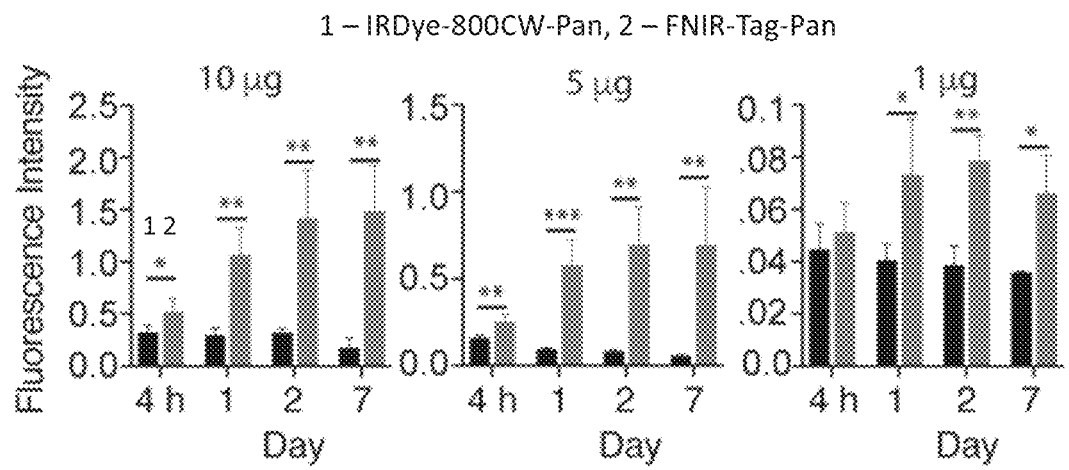
FIG. 20 is a series of graphs showing tumor signal (total radiance, all values×$10^9$, normalized to tumor size) for MDA-MB-468 tumor-bearing mice injected with 10 μg, 5 μg, and 1 μg of DOL 4 IRDye®-800CW and FNIR-Tag conjugates at 4 hours, 1 day, 2 days and 7 days post-injection (*$p>0.5$, $p<0.01$, *$p<0.001$).
Figure 21:
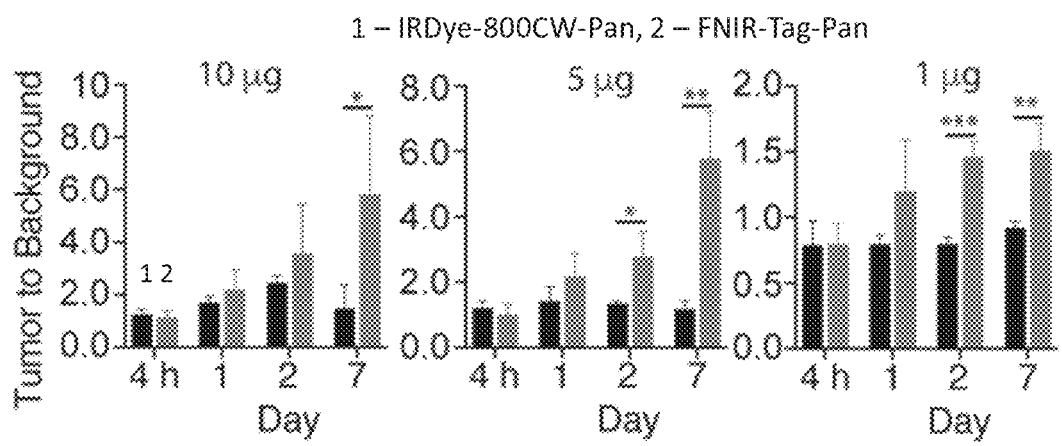
FIG. 21 is a series of graphs showing tumor to background ratio for MDA-MB-468 tumor-bearing mice injected with 10 μg, 5 μg, and 1 μg of DOL 4 IRDye®-800CW and FNIR-Tag conjugates at 4 hours, 1 day, 2 days and 7 days post-injection (*$p>0.5$, $p<0.01$, *$p<0.001$).
Figure 22:
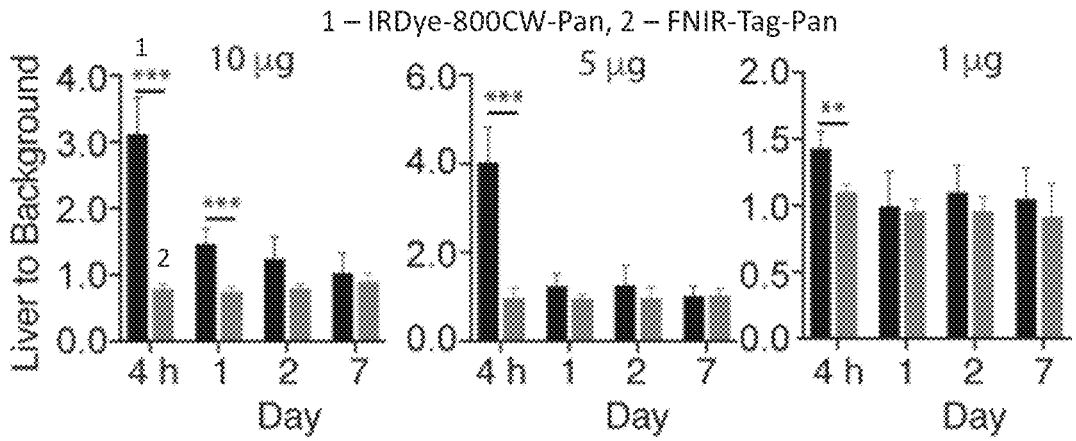
FIG. 22 is a series of graphs showing liver to background ratio for MDA-MB-468 tumor-bearing mice injected with 10 μg, 5 μg, and 1 μg of DOL 4 IRDye®-800CW and FNIR-Tag conjugates at 4 hours, 1 day, 2 days and 7 days post-injection (*$p>0.5$, $p<0.01$, *$p<0.001$).

A dose lowering study with the goal of defining an optimal dose for FNIR-Tag conjugates was performed. Three doses, 10 μg, 5 μg, and 1 μg, which span the lower end of the doses used in prior studies, were examined. Dorsal and ventral images (FIGS. 18 and 19, respectively) of tumor bearing mice were collected before and 0, 4 h, 1 day, 2 day, and 7 days after tail injection of 10, 5 and 1 μg of IRDye®-800CW and FNIR-Tag conjugates (DOL 4) (n=4 per group). Clearly discernable signals using FNIR-Tag conjugates were observed throughout the dosage range, while IRDye®-800CW conjugate tumor signal could not be visualized below 5 μg. In quantifying the images, significantly higher fluorescence intensity was observed from the FNIR-Tag conjugates in nearly all studies FIG. 20 (total radiance, all values×$10^9$, normalized to tumor size) (*p>0.5,  p<0.01, *p<0.001). Significantly improved tumor to background ratio was observed for the 10 μg, 5 μg, and 1 μg doses of FNIR-Tag conjugates relative to IRDye®-800CW conjugates starting on day 2, with values reaching 5.78 at day 7 with a 5 μg dose (FIG. 21 (*p>0.5, p<0.01, *p<0.001)). Dramatically higher liver to background ratios were observed for the 10 μg, and 5 μg doses of IRDye®-800CW conjugates at 4 hour and day 1 time points (FIG. 22 (*p>0.5, p<0.01, *p<0.001)). The observation that FNIR-Tag antibody conjugates are less subject to hepatobiliary uptake is likely to be of significant utility, particularly in instances that seek to visualize events in this region.

Example 5

Tumor Visualization with the Disclosed Conjugates

A subject having a tumor is identified and selected. The subject may be selected based on a clinical presentation and/or by performing tests to demonstrate presence of a tumor.

The subject is treated by administering a conjugate as disclosed herein, or a pharmaceutical composition thereof, at a dose determined by a clinician to be effective for tumor visualization. The conjugate is administered by any suitable means, such as parenteral, intravenous, or subcutaneous injection. In some instances, the conjugate is injected directly into the tumor. In some examples, the location of the conjugate is monitored by exposure to light having a wavelength suitable for inducing fluorescence of the cyanine fluorophore, thereby exciting the cyanine fluorophore, and detecting fluorescence of the conjugate. Monitoring may be performed after a period of time sufficient to allow binding of the conjugate to the tumor. The administered conjugate may be irradiated by targeted application of an effective quantity of light having a wavelength in the near-infrared range and a selected intensity to a targeted portion of the subject. Irradiation is performed externally or internally. When external irradiation is desired, the surface area can be controlled with an appropriate light applicator, e.g., a microlens, Fresnel lens, or diffuser. When internal radiation is desired, an endoscope or a fiber optic catheter may be used. Advantageously, the targeted portion of the subject is proximate the tumor. In some instances, irradiation may be performed several hours to several days after administration of the conjugate, such as from 1-7 days after administration of the conjugate.

At least a portion of the tumor may be surgically excised following administration of the conjugate. Fluorescence-guided surgery is used to determine the location and extent of tissue excision.

In some cases, the subject is suspected of having a tumor and presence of a tumor is confirmed by administering the conjugate to the subject and monitoring the conjugate's fluorescence at a suspected tumor site. Accumulation of the conjugate and fluorescence at the suspected tumor site diagnoses presence of a tumor.

A therapeutically effective amount of a second agent may be co-administered with the conjugate or salt thereof. The conjugate and the second agent may be administered either separately or together in a single composition. The second agent may be administered by the same route or a different route. If administered concurrently, the conjugate and the second agent may be combined in a single pharmaceutical composition or may be administered concurrently as two pharmaceutical compositions. The second agent may be, for example, an anti-tumor agent or an angiogenesis inhibitor.

Example 6

Compound Synthesis and Characterization

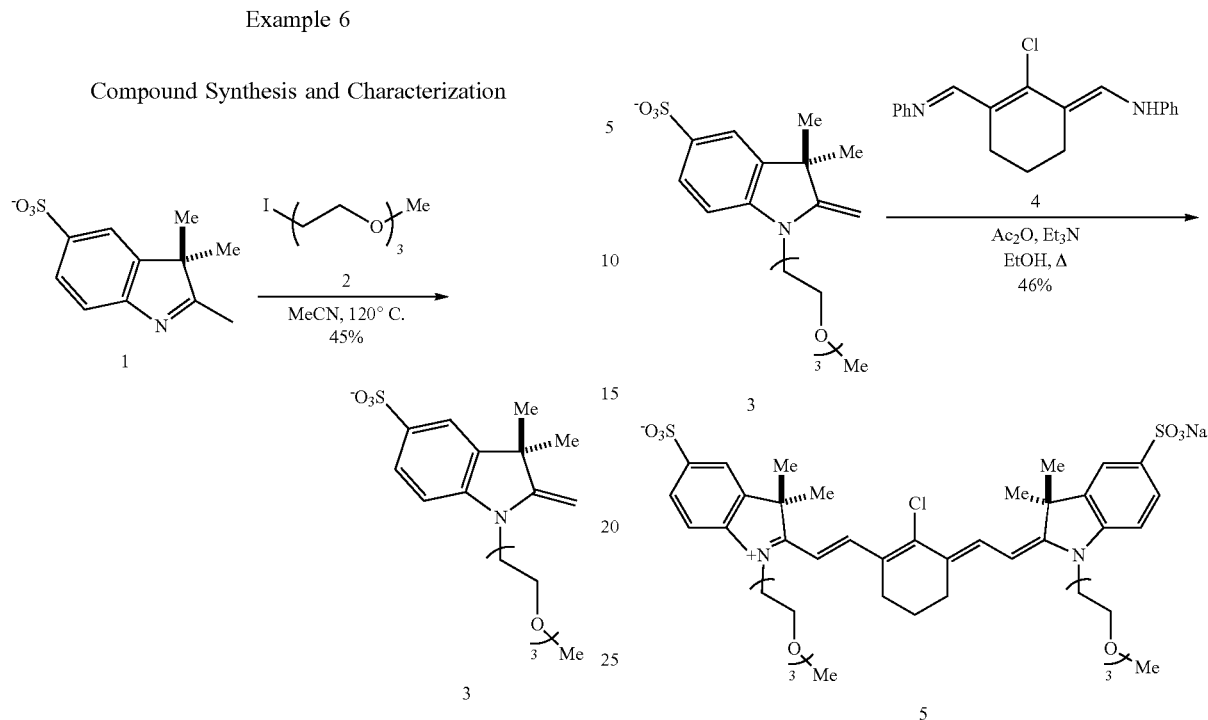

(3): To a microwave vial equipped with a magnetic stir bar was added indolenine 1 (3.0 g, 10.8 mmol; Park et al., *Bioconjugate Chem.* 2012, 23:350), MeCN (12 mL) and iodide 2 (3.0 g, 10.8 mmol; Lawal et al., *Supramol. Chem.* 2009, 21:55). The vessel was sealed under argon and the light brown slurry was heated to 120° C. in a sand bath for 22 hours during which time the reaction changed to a deep red/pink color. The reaction was cooled and the solvent removed by rotary evaporation. Water (10 mL) was added to the red crude and purified by reversed-phase chromatography ($C_{18}$ Aq, 0→30% MeCN/water). The product-containing fractions were combined and the solvent removed by rotary evaporation to afford 3 (2.1 g, 45% yield) as a red gummy solid. $^1$H NMR (400 MHz, DMSO-$d_6$ exists as 93:7 ratio of enamineimine tautomers) δ 7.38-7.29 (m, 2H), 6.59 (d, J=8.0 Hz, 1H), 3.96 (d, J=1.9 Hz, 1H), 3.88 (d, J=1.9 Hz, 1H), 3.68 (t, J=6.0 Hz, 2H), 3.57 (t, J=6.0 Hz, 2H), 3.52-3.43 (m, 6H), 3.41-3.36 (m, 2H), 3.22 (s, 3H), 1.26 (s, 6H); $^{13}$C NMR (125 MHz, DMSO-$d_6$) δ 160.6, 145.7, 139.3, 135.7, 125.3, 119.4, 104.2, 74.7, 71.2, 70.1, 69.8, 69.6, 66.4, 58.0, 43.5, 41.9, 29.7; IR (thin film) 2921, 1715, 1650, 1604, 1486, 1382, 1182 cm$^{-1}$; HRMS (ESI) calculated for $C_{18}H_{28}NO_6S$ (M+H)$^+$ 386.1632, observed 386.1632.

(5): To a microwave tube equipped with a magnetic stir bar was added indolenine 3 (2.07 g, 4.9 mmol) in ethanol (14 mL) and chloride 4 (0.45 g, 1.4 mmol). The vessel was sealed and flushed with argon. Triethylamine (1.37 mL, 9.8 mmol), and acetic anhydride (1.85 mL, 19.6 mmol) were then added in succession by syringe. The yellow solution was heated to 120° C. for 30 minutes, during which time the reaction transitioned to a deep green color. The reaction was cooled and the solvent removed by rotary evaporation. Saturated aqueous NaHCO$_3$ (17 mL) was added and the green residue was purified by reversed-phase chromatography ($C_{18}$, 0→30% MeCN/water). The product-containing fractions were lyophilized to afford 5 (1.04 g, 46% yield) as a green solid. $^1$H NMR (500 MHz, methanol-$d_4$) δ 8.46 (d, J=14.1 Hz, 2H), 7.92 (d, J=1.7 Hz, 2H), 7.88 (dd, J=8.3, 1.7 Hz, 2H), 7.40 (d, J=8.4 Hz, 2H), 6.49 (d, J=14.1 Hz, 2H), 4.41 (t, J=5.1 Hz, 4H), 3.91 (t, J=5.1 Hz, 4H), 3.60-3.57 (m, 4H), 3.53-3.50 (m, 4H), 3.48-3.44 (m, 4H), 3.41-3.37 (m, 4H), 3.28 (s, 6H), 2.75 (t, J=6.2 Hz, 4H), 2.00-1.91 (m, 2H), 1.77 (s, 12H); $^{13}$C NMR (125 MHz, methanol-$d_4$) δ 175.6, 151.4, 145.7, 145.3, 143.6, 142.4, 129.0, 128.0, 121.3, 112.4, 104.2, 72.9, 72.1, 71.7, 71.4, 69.2, 59.1, 50.7, 46.1, 28.3, 27.4, 22.1; IR (thin film) 2864, 1546, 1509, 1427, 1387, 1234, 1151 cm$^{-1}$; HRMS (ESI) calculated for $C_{44}H_{60}ClN_2O_{12}S_2$ (M+H)$^+$ 907.3271, observed 907.3268.

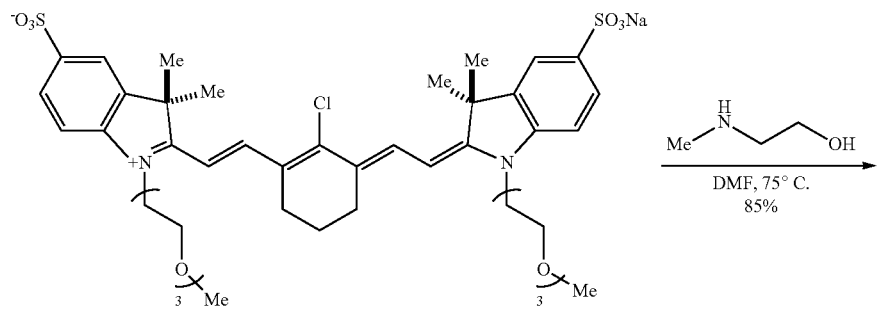

-continued

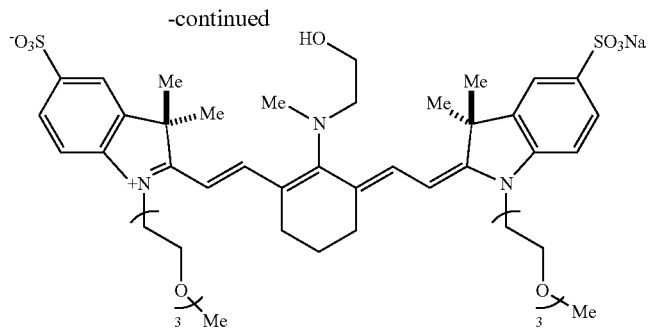

6

(6): To a 1-dram vial equipped with a magnetic stir bar was added chloride 5 (100 mg, 0.108 mmol) and DMF (1.0 mL). 2-(Methylamino)-ethanol (35 μL, 0.43 mmol) was added and the reaction was heated to 75° C. for 15 minutes, during which time the reaction color transitioned from green to dark blue. The reaction was cooled and diluted with saturated aqueous $NaHCO_3$ (3 mL) and $H_2O$ (7 mL), and the solution was directly purified by reversed-phase chromatography ($C_{18}$ Aq gold, 0→25% MeCN/water). The product-containing fractions were lyophilized to afford 6 (90 mg, 85% yield) as a blue solid. $^1$H NMR (400 MHz, methanol-$d_4$) δ 7.89-7.64 (m, 6H), 7.16 (d, J=8.5 Hz, 2H), 6.05 (d, J=13.2 Hz, 2H), 4.27-4.11 (m, 4H), 4.01-3.92 (m, 4H), 3.89-3.81 (m, 4H), 3.61-3.57 (m, 4H), 3.57-3.51 (m, 7H), 3.51-3.46 (m, 4H), 3.45-3.40 (m, 4H), 3.30 (s, 6H), 2.63-2.45 (m, 4H), 1.92-1.79 (m, 2H), 1.67 (s, 12H); $^{13}$C NMR (125 MHz, DMSO-$d_6$) δ 176.1, 168.1, 143.2, 143.2, 140.7, 139.1, 125.7, 123.3, 119.3, 108.7, 95.9, 71.2, 70.3, 69.8, 69.7, 67.3, 59.6, 58.5, 58.0, 47.2, 44.1, 43.3, 28.7, 24.4, 21.5; IR (thin film) 3409, 2927, 2870, 1546, 1509, 1365, 1279, 1158 cm$^{-1}$; HRMS (ESI) calculated for $C_{47}H_{68}N_2O_{13}S_2$ (M+H)$^+$ 946.4188, observed 946.4186.

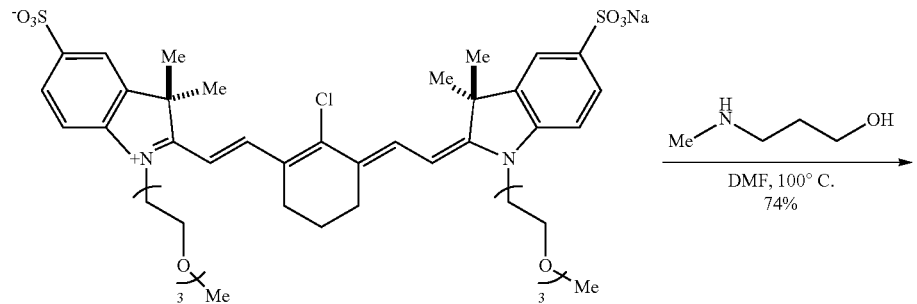

5

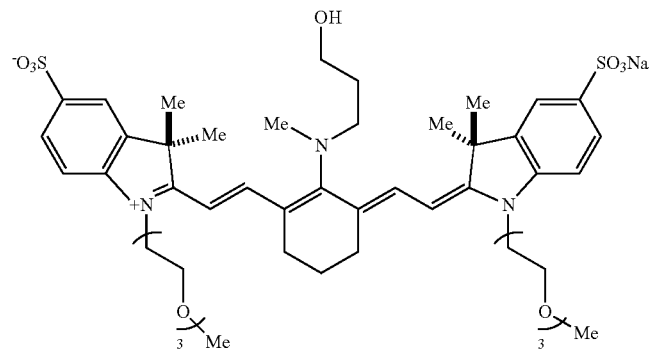

7

(7): To a 1-dram vial equipped with a magnetic stir bar was added chloride 5 (640 mg, 0.65 mmol) and DMF (18 mL). 3-(Methylamino)-1-propanol (250 μL, 2.54 mmol) was added and the reaction was heated to 100° C. for 25 minutes, during which time the reaction color transitioned from green to dark blue. The reaction was cooled and diluted with saturated aqueous $NaHCO_3$ (18 mL) and the solution was directly purified by reversed-phase chromatography ($C_{18}$ Aq gold, 0→40% MeCN/water). The product-containing fractions were lyophilized to afford 7 (616 mg, 74% yield) as a blue solid. $^1$H NMR (500 MHz, DMSO-$d_6$) δ 7.62 (d, J=1.7 Hz, 2H), 7.55 (dd, J=8.2, 1.7 Hz, 2H), 7.46 (d, J=13.3 Hz, 2H), 7.12 (d, J=8.3 Hz, 2H), 5.98 (d, J=13.3 Hz, 2H), 4.61 (t, J=4.7 Hz, 1H), 4.24-4.14 (m, 4H), 3.90-3.80 (m, 2H), 3.78-3.69 (m, 4H), 3.53-3.50 (m, 4H), 3.49-3.39 (m, 14H), 3.33 (s, 3H), 3.18 (s, 6H), 2.49-2.46 (m, 4H), 1.91 (p, J=6.0 Hz, 2H), 1.74 (p, J=6.7 Hz, 2H), 1.58 (s, 12H); $^{13}$C NMR (125 MHz, DMSO-$d_6$) δ 174.9, 168.2, 143.3, 143.2, 140.4, 139.0, 125.8, 123.3, 119.4, 108.8, 96.0, 71.2, 70.3, 69.8, 69.7, 67.3, 58.1, 58.0, 55.6, 47.2, 44.8, 43.4, 31.5, 28.7, 24.3, 21.4; IR (thin film) 3410, 2926, 2870, 1543, 1366, 1279, 1160 cm$^{-1}$; HRMS (ESI) calculated for $C_{48}H_{70}N_3O_{13}S_2$ (M+H)$^+$ 960.4345, observed 960.4343.

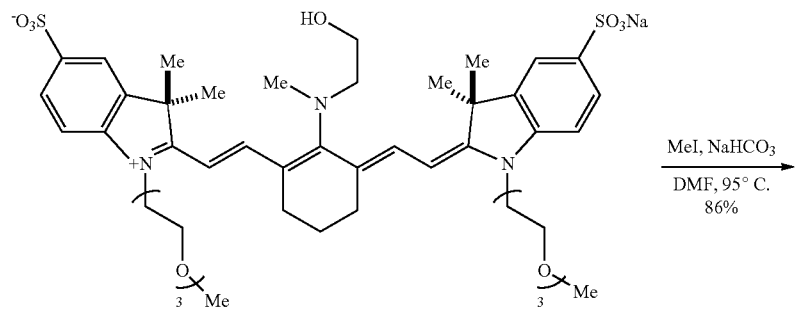

(8): To a microwave vial equipped with a magnetic stir bar was added cyanine 6 (70 mg, 0.11 mmol) and $NaHCO_3$ (61 mg, 0.72 mmol). DMF (1.5 mL) and methyl iodide (45 μL, 0.72 mmol) were added and the reaction was heated to 95° C. for 2 hours, during which time the reaction color transitioned from blue to green. The reaction was cooled and diluted with water (10 mL) and the solution was directly purified by reversed-phase chromatography ($C_{18}$ Aq gold, 0→30% MeCN/water). The product-containing fractions were lyophilized to afford 8 (60 mg, 86% yield) as a green solid. $^1$H NMR (500 MHz, DMSO-$d_6$) δ 7.87 (d, J=14.1 Hz, 2H), 7.74 (s, 2H), 7.67-7.59 (m, 2H), 7.35 (d, J=8.3 Hz, 2H), 6.29 (d, J=14.2 Hz, 2H), 4.47 (t, J=6.1 Hz, 2H), 4.39 (t, J=5.3 Hz, 4H), 3.95 (t, J=6.3 Hz, 2H), 3.79 (t, J=5.1 Hz, 4H), 3.54-3.48 (m, 4H), 3.45-3.35 (m, 12H), 3.31 (s, 9H), 3.18 (s, 6H), 2.60 (t, J=6.2 Hz, 4H), 1.85-1.73 (m, 2H), 1.67 (s, 12H); $^{13}$C NMR (125 MHz, DMSO-$d_6$) δ 172.2, 167.9, 145.3, 142.4, 140.1, 139.1, 126.0, 122.4, 119.5, 110.7, 101.0, 71.2, 70.3, 69.8, 69.6, 69.4, 67.5, 64.1, 58.0, 53.4, 48.6, 44.3, 27.8, 24.2, 20.5; IR (thin film) 2868, 1556, 1504, 1392, 1357, 1249, 1148 cm$^{-1}$; HRMS (ESI) calculated for $C_{49}H_{72}N_3O_{13}S_2$ (M+H)$^+$ 974.4501, observed 974.4506.

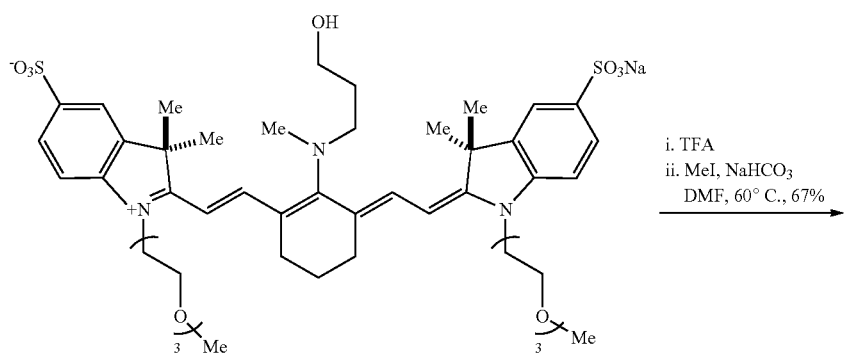

7

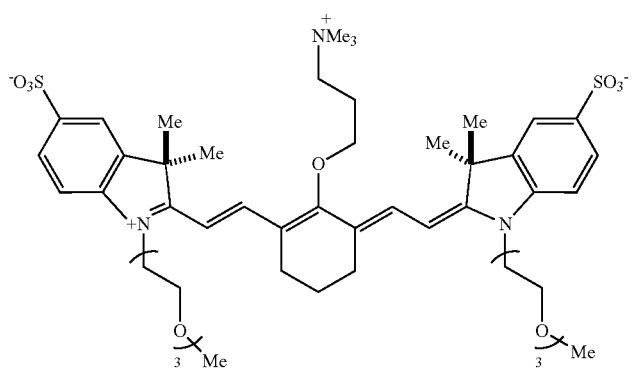

9

(9, UL-766): To a round bottom flask equipped with a magnetic stir bar was added cyanine 7 (620 mg, 0.11 mmol) and TFA (6 mL). The red solution was heated to 60° C. for 5 minutes under argon. The TFA was removed in vacuo and the residue was placed under vacuum (<0.1 Torr) for 5 minutes. DMF (20 mL), NaHCO$_3$ (2.6 g) and methyl iodide (2 mL) were added and the reaction was heated to 60° C. for 3 hours. The reaction was cooled and diluted with water (40 mL) and the solution was directly purified by reversed-phase chromatography (C$_{18}$ Aq gold, 0→40% MeCN/water). The product-containing fractions were lyophilized to afford 9 (420 mg, 67% yield) as a green solid. $^1$H NMR (500 MHz, DMSO-d$_6$) δ 7.94 (d, J=14.2 Hz, 2H), 7.80 (d, J=1.8 Hz, 2H), 7.63 (dd, J=8.1, 1.8 Hz, 2H), 7.33 (d, J=8.3 Hz, 2H), 6.28 (d, J=14.2 Hz, 2H), 4.37 (t, J=5.3 Hz, 4H), 4.03 (t, J=5.6 Hz, 2H), 3.79 (t, J=5.1 Hz, 4H), 3.76-3.70 (m, 2H), 3.53-3.49 (m, 5H), 3.44-3.36 (m, 8H), 3.33-3.30 (m, 4H), 3.26 (s, 9H), 3.18 (s, 6H), 2.62-2.54 (m, 4H), 2.44-2.36 (m, 2H), 1.84-1.76 (m, 2H), 1.69 (s, 12H); $^{13}$C NMR (125 MHz, DMSO-d$_6$) δ 172.2, 168.5, 145.2, 142.4, 140.1, 139.5, 126.0, 122.3, 119.7, 110.6, 100.8, 73.4, 71.2, 70.3, 69.8, 69.7, 67.5, 62.9, 58.0, 52.4, 48.6, 44.2, 39.5, 27.9, 24.2, 23.8, 20.7; IR (thin film) 2874, 1557, 1506, 1392, 1359, 1248, 1151 cm$^{-1}$; HRMS (ESI) calculated for C$_{50}$H$_{74}$N$_3$O$_{13}$S$_2$ (M+H)$^+$ 988.4658, observed 988.4660.

The spectroscopic properties of compounds 8 and 9 were evaluated and compared to another heptamethine cyanine—FNIR-774. The results are presented in Table 1. Compounds 8 and 9 also demonstrated excellent water solubility of up to 5 mM in pH 7.4 PBS.

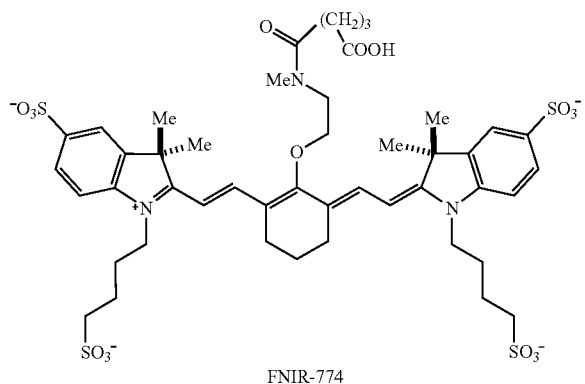

FNIR-774

TABLE 1

| | $\lambda_{max}$ (nm) | ε (M$^{-1}$cm$^{-1}$) | $\lambda_{em}$ (nm) | $\Phi_F$ | brightness (ε × $\Phi_F$) |
|---|---|---|---|---|---|
| FNIR-774 | 774 | 204,000 | 789 | 0.10 | 21,000 |
| 8 | 774 | 255,000 | 796 | 0.067 | 17,000 |
| 9 | 766 | 229,000 | 789 | 0.095 | 22,000 |

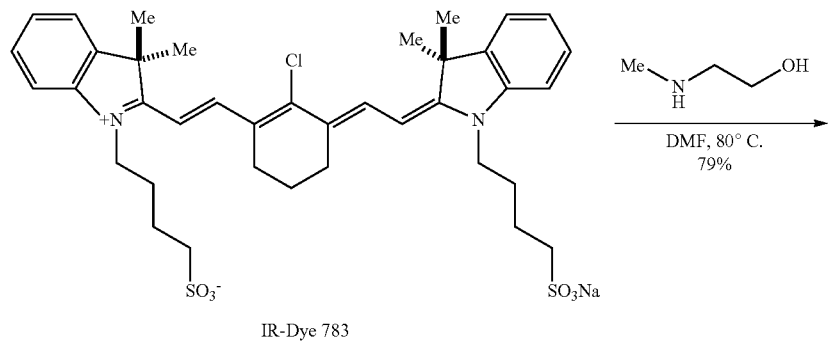

IR-Dye 783

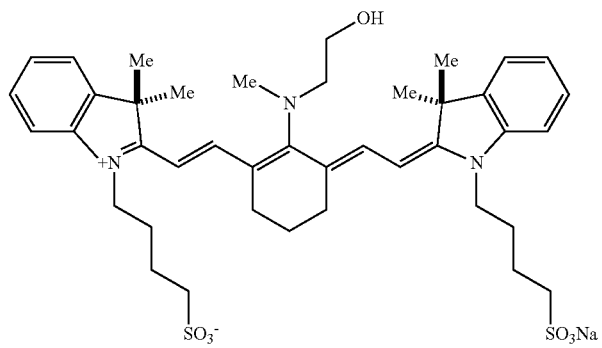

BL-760 Intermediate

BL-760 Intermediate. Commercially available IR Dye 783 (120 mg, 0.16 mmol) was dissolved in dry DMF (2 mL) in a microwave tube equipped with a magnetic stir bar and sealed. The solution was flushed with argon for 2 min, followed by addition of 2-(methylamino)ethanol (65 µl, 0.8 mmol). The solution was heated to 80° C. in a sand bath during which time the color changed from green to blue and LC-MS indicated formation of the desired product. The reaction mixture was cooled, precipitated into Et$_2$O and centrifuged for 3 min at 4500 rpm. Water (2 mL) and aqueous saturated NaHCO$_3$ solution (2 mL) were added to the pellet and the residue was purified by reversed-phase chromatography (C$_{18}$, 0→40% MeCN/H$_2$O). The product containing fractions were combined and lyophilized to afford BL-760 intermediate (99 mg, 79% yield) as a blue solid. $^1$H NMR (400 MHz, Methanol-d$_4$) δ 7.77 (d, J=13.3 Hz, 1H), 7.37 (d, J=7.4 Hz, 1H), 7.32 (t, J=7.7 Hz, 1H), 7.16 (d, J=8.0 Hz, 1H), 7.11 (t, J=7.5 Hz, 1H), 5.96 (d, J=13.4 Hz, 1H), 4.1-4.0 (m, 4H), 3.95-3.85 (m, 4H), 3.53-3.39 (m, 4H), 2.87 (t, J=6.8 Hz, 4H), 2.55 (t, J=6.6 Hz, 4H), 2.05-1.86 (m, 8H), 1.85 (t, J=6.5 Hz, 2H), 1.65 (s, 12H) ppm.

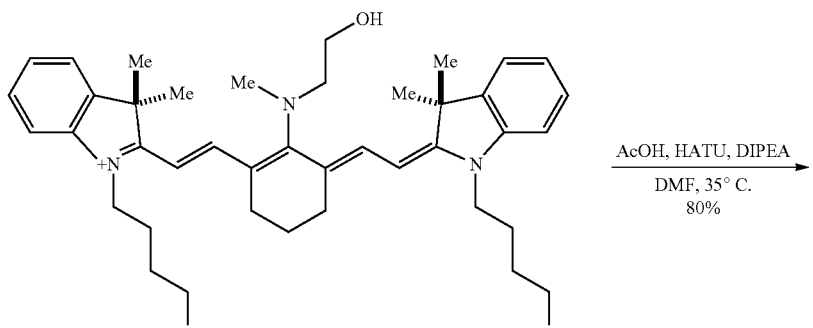

BL-760 Intermediate

-continued

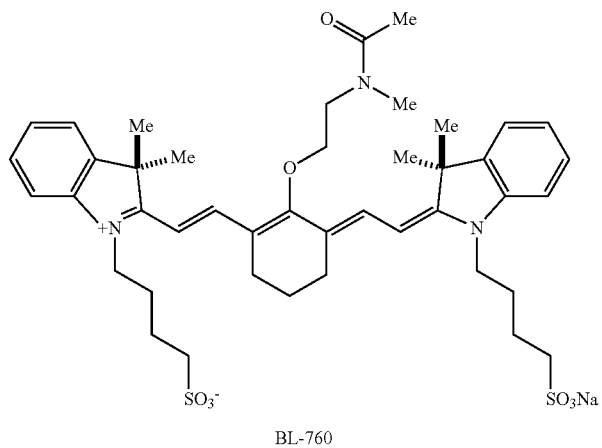

BL-760

BL-760. HATU (61 mg, 0.16 mmol), acetic acid (10 μl, 0.17 mmol) and dry DMF (2.8 mL) were added to a 1-dram vial and flushed with argon. DIPEA (31 μl, 0.17 mmol) was added and the solution was stirred at r.t. for 10 min. In a separate 1-dram vial, BL-760 Intermediate was dissolved in dry DMF (2.1 mL) and flushed with argon. To this solution was added 1.4 mL of the activated ester solution and the solution was heated to 35° C. in a sand bath overnight, during which time the color changed from blue to green. The solution was cooled, precipitated into Et$_2$O and centrifuged for 3 min at 4500 RPM. The pellet was dissolved in water (5 mL) and the solution was directly purified by reversed-phase chromatography (C$_{18}$, 0→40% MeCN/H$_2$O). The product containing fractions were combined and lyophilized to afford BL-760 (53 mg, 80% yield) as a bluish green solid. $^1$H NMR (400 MHz, Methanol-d$_4$, compound exists as a mixture of rotamers, major rotamer is designated by *, minor rotamer denoted by §) δ 8.14 (two overlapping d, J=14.2 Hz, 2H*, 2H$^§$), 7.49 (dd, J=7.5, 1.1 Hz, 2H*, 2H$^§$), 7.44-7.37 (m, 2H*, 2H$^§$), 7.35-7.31 (m, 2H*, 2H$^§$), 7.24 (tdd, J=7.4, 1.9, 1.0 Hz, 2H*, 2H$^§$), 6.22 (d, J=5.9 Hz, 2H*), 6.19 (d, J=5.8 Hz, 2H$^§$), 4.25-4.08 (m, 6H*, 6H$^§$), 4.07-3.87 (m, 2H*, 2H$^§$), 3.29 (s, 3H*), 3.20 (s, 3H$^§$), 2.88 (td, J=7.2, 1.7 Hz, 4H*, 4H$^§$), 2.66 (q, J=5.7 Hz, 4H*, 4H$^§$), 2.29 (s, 3H*), 2.22 (s, 3H$^§$), 2.03-1.89 (m, 10H*, 10H$^§$), 1.74 (s, 12H*), 1.70 (s, 12H$^§$) ppm.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A conjugate or conjugate precursor, or stereoisomer thereof, according to Formula I:

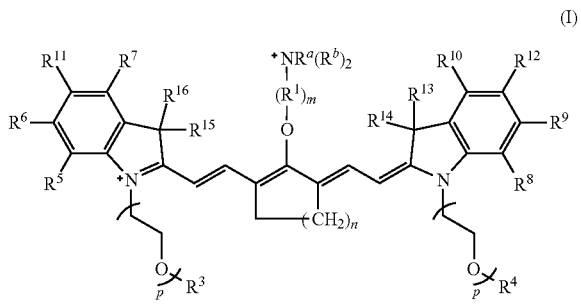

wherein m is 3, 4, or 5;

n is 1, 2, or 3;

each p independently is 1, 2, 3, 4, 5, 6, 7, 8, 9, or 10;

R$^1$ is —CR$^2_2$— where each R$^2$ independently is H, halo, optionally substituted aliphatic, or optionally substituted aryl;

R$^3$ and R$^4$ independently are aliphatic;

R$^5$ to R$^{10}$ independently are H or aliphatic;

R$^{11}$ and R$^{12}$ independently are a sulfonate-containing group;

R$^{13}$ to R$^{16}$ independently are aliphatic;

R$^a$ is —(R$^1$)$_q$C(O)R$^c$ where q is 1, 2, 3, 4, 5, 6, 7, 8, 9, or 10;

each R$^b$ independently is C$_1$-C$_5$ aliphatic; and

R$^c$ is a targeting agent-containing group,

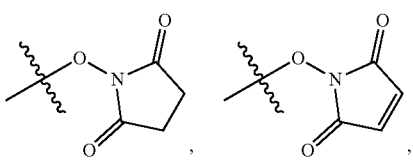

-continued

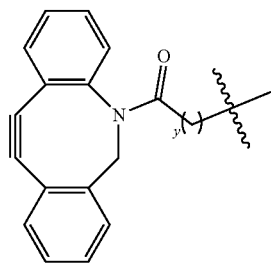

where y is an integer≥1, or —OH, wherein the targeting agent is an antibody, a peptide, a protein, an amino acid, a nucleoside, a nucleotide, a nucleic acid, an oligonucleotide, a carbohydrate, a lipid, a hapten, or a receptor ligand.

2. The conjugate or conjugate precursor of claim 1, wherein:
each $R^2$ independently is H, halo, optionally substituted alkyl, or optionally substituted aryl;
$R^3$ and $R^4$ independently are alkyl;
$R^5$ to $R^{10}$ independently are H or alkyl;
$R^{11}$ and $R^{12}$ independently are a sulfonate-containing group, H, or alkyl; and
$R^{13}$ to $R^{16}$ independently are alkyl.

3. The conjugate or conjugate precursor of claim 1, wherein the targeting agent is an antibody.

4. The conjugate or conjugate precursor of claim 3, wherein the antibody is panitumumab or trastuzumab.

5. The conjugate or conjugate precursor of claim 1, wherein:
$R^3$ and $R^4$ are the same;
$R^5$ and $R^8$ are the same;
$R^6$ and $R^9$ are the same;
$R^7$ and $R^{10}$ are the same;
$R^{11}$ and $R^{12}$ are the same; and
$R^{13}$-$R^{16}$ are the same.

6. The conjugate or conjugate precursor of claim 1, wherein:
$R^5$-$R^{10}$ are H; and
$R^{11}$ and $R^{12}$ are sulfonate.

7. The conjugate or conjugate precursor of claim 1, wherein:
(i) n is 2; or
(ii) p is 2, 3, or 4; or
(iii) q is 2, 3, or 4; or
(iv) any combination of (i), (ii) and (iii).

8. The conjugate or conjugate precursor of claim 1, wherein:
(I) $R^3$ and $R^4$ are methyl; or
(ii) $R^{13}$-$R^{16}$ are methyl; or
(iii) each $R^b$ is methyl; or
(iv) any combination of (i), (ii), and (iii).

9. The conjugate of claim 1 according to Formula II:

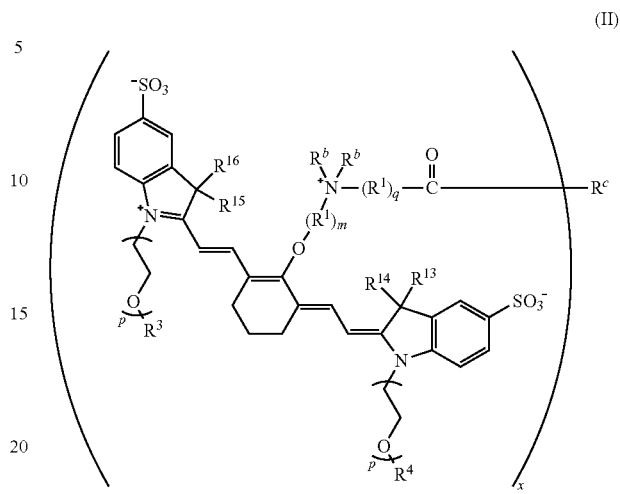

(II)

wherein x is 2, 3, 4, 5, 6, 7, or 8; and
$R^c$ is a targeting agent-containing group of claim 1.

10. The conjugate of claim 9, where $R^c$ is —N(H)Ab where Ab is an antibody.

11. The conjugate of claim 9, wherein:
(i) $R^3$ and $R^4$ are methyl; or
(ii) $R^{13}$-$R^{16}$ are methyl; or
(iii) each $R^b$ is methyl; or
(iv) p is 2, 3, or 4; or
(v) q is 2, 3, or 4; or
(vi) any combination of (i), (ii), (iv), and (v).

12. A pharmaceutical composition, comprising:
a conjugate according to claim 1; and
a pharmaceutically acceptable carrier.

13. A method of tumor imaging in a subject or a sample comprising:
contacting a biological sample including or suspected of including a target with a conjugate according to claim 1, wherein $R^c$ is a targeting agent-containing group, the targeting agent recognizing and binding to the target;
subsequently irradiating the biological sample with a quantity of light having a selected wavelength and selected intensity to induce fluorescence of the conjugate, wherein the wavelength is from 650 nm, to 900 nm; and
detecting fluorescence of the irradiated biological sample, wherein fluorescence indicates presence of the target in the biological sample.

14. The method of claim 13, wherein detecting fluorescence of the biological sample is performed ex vivo.

15. The method of claim 14, wherein contacting the biological sample with the conjugate is performed in vivo by administering the conjugate or a pharmaceutical composition comprising the conjugate to a subject.

16. The method of claim 15, wherein:
irradiating the biological sample comprises irradiating a target area of the subject; and
detecting fluorescence comprises obtaining an image of the irradiated target area, wherein fluorescence in the image indicates presence of the target in the target area.

17. The method of claim 16, wherein the target area is an area in which the tumor is located.

18. The method of claim 17, further comprising excising fluorescent tumor cells from the target area.

19. The method of claim 13, wherein the targeting agent is an antibody.

* * * * *